(12) United States Patent
Heldreth et al.

(10) Patent No.: US 10,729,551 B2
(45) Date of Patent: *Aug. 4, 2020

(54) ORTHOPAEDIC KNEE PROSTHESIS HAVING CONTROLLED CONDYLAR CURVATURE

(71) Applicant: DEPUY IRELAND UNLIMITED COMPANY, Cork (IE)

(72) Inventors: Mark A. Heldreth, Mentone, IN (US); Daniel D. Auger, Fort Wayne, IN (US); Joseph G. Wyss, Fort Wayne, IN (US); Danny W. Rumple, Jr., Warsaw, IN (US); Christel M. Wagner, Plymouth, IN (US); Dimitri Sokolov, Campbell, CA (US); Jordan S. Lee, Warsaw, IN (US); John L. Williams, Fort Wayne, IN (US); Said T. Gomaa, Fort Wayne, IN (US); John M. Armacost, Warsaw, IN (US)

(73) Assignee: DePuy Ireland Unlimited Company, Ringaskiddy, County Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,386

(22) Filed: Jan. 7, 2019

(65) Prior Publication Data
US 2019/0133772 A1    May 9, 2019

Related U.S. Application Data

(63) Continuation of application No. 15/402,513, filed on Jan. 10, 2017, now Pat. No. 10,179,051, which is a
(Continued)

(51) Int. Cl.
*A61F 2/38* (2006.01)
*A61F 2/30* (2006.01)

(52) U.S. Cl.
CPC ............ *A61F 2/3836* (2013.01); *A61F 2/38* (2013.01); *A61F 2/3859* (2013.01); *A61F 2/3868* (2013.01); *A61F 2002/30245* (2013.01)

(58) Field of Classification Search
CPC ......... A61F 2/38; A61F 2/3859; A61F 2/3836
See application file for complete search history.

(56) References Cited

U.S. PATENT DOCUMENTS 3,765,033 A   10/1973 Goldberg et al.
3,840,905 A   10/1974 Deane
(Continued)

FOREIGN PATENT DOCUMENTS

CN   1803106 A    7/2006
CN   1872009 A   12/2006
(Continued)

OTHER PUBLICATIONS

Ries, "Effect of ACL Sacrifice, Retention, or Substitution on K After TKA," http://www.orthosupersite.com/view.asp?rID=23134, Aug. 2007, 5 pgs.
(Continued)

*Primary Examiner* — Jason-Dennis N Stewart
(74) *Attorney, Agent, or Firm* — Barnes & Thornburg LLP

(57) ABSTRACT

An orthopaedic knee prosthesis includes a femoral component having a condyle surface. The condyle surface is defined by one or more radii of curvatures, which are controlled to reduce or delay the onset of anterior translation of the femoral component relative to a tibial bearing.

12 Claims, 11 Drawing Sheets

Related U.S. Application Data continuation of application No. 14/309,466, filed on Jun. 19, 2014, now Pat. No. 9,539,099, which is a continuation of application No. 13/540,177, filed on Jul. 2, 2012, now Pat. No. 8,795,380, which is a continuation of application No. 12/488,107, filed on Jun. 19, 2009, now Pat. No. 8,236,061.

(60) Provisional application No. 61/077,124, filed on Jun. 30, 2008.

(56) References Cited

U.S. PATENT DOCUMENTS

| | | |
|---|---|---|
| 3,852,045 A | 12/1974 | Wheeler et al. |
| 3,855,638 A | 12/1974 | Pilliar |
| 3,869,731 A | 3/1975 | Waugh et al. |
| 4,081,866 A | 4/1978 | Upshaw et al. |
| 4,156,943 A | 6/1979 | Collier |
| 4,206,516 A | 6/1980 | Pilliar |
| 4,209,861 A | 7/1980 | Walker et al. |
| 4,215,439 A | 8/1980 | Gold et al. |
| 4,249,270 A | 2/1981 | Bahler et al. |
| 4,257,129 A | 3/1981 | Volz |
| 4,262,368 A | 4/1981 | Lacey |
| 4,340,978 A | 7/1982 | Buechel et al. |
| 4,470,158 A | 9/1984 | Pappas et al. |
| 4,612,160 A | 9/1986 | Donlevy et al. |
| 4,673,407 A | 6/1987 | Martin |
| 4,714,474 A | 12/1987 | Brooks et al. |
| 4,795,468 A | 1/1989 | Hodorek et al. |
| 4,808,185 A | 2/1989 | Penenberg et al. |
| 4,822,362 A | 4/1989 | Walker et al. |
| 4,838,891 A | 6/1989 | Branemark et al. |
| 4,888,021 A | 12/1989 | Forte et al. |
| 4,938,769 A | 7/1990 | Shaw |
| 4,944,757 A | 7/1990 | Martinez et al. |
| 4,944,760 A | 7/1990 | Kenna |
| 4,950,298 A | 8/1990 | Gustilo et al. |
| 4,963,152 A | 10/1990 | Hofmann et al. |
| 4,990,163 A | 2/1991 | Ducheyne et al. |
| 5,007,933 A | 4/1991 | Sidebotham et al. |
| 5,011,496 A | 4/1991 | Forte et al. |
| 5,019,103 A | 5/1991 | Van Zile et al. |
| 5,037,423 A | 8/1991 | Kenna |
| 5,071,438 A | 12/1991 | Jones et al. |
| 5,080,675 A | 1/1992 | Ashby et al. |
| 5,104,410 A | 4/1992 | Chowdhary |
| 5,108,442 A | 4/1992 | Smith |
| 5,116,375 A | 5/1992 | Hofmann |
| 5,133,758 A | 7/1992 | Hollister |
| 5,147,405 A | 9/1992 | Van Zile et al. |
| 5,171,283 A | 12/1992 | Pappas et al. |
| 5,201,766 A | 4/1993 | Georgette |
| 5,219,362 A | 6/1993 | Tuke et al. |
| 5,236,461 A | 8/1993 | Forte |
| 5,251,468 A | 10/1993 | Lin et al. |
| 5,258,044 A | 11/1993 | Lee |
| 5,271,737 A | 12/1993 | Baldwin et al. |
| 5,282,861 A | 2/1994 | Kaplan |
| 5,308,556 A | 5/1994 | Bagley |
| 5,309,639 A | 5/1994 | Lee |
| 5,326,361 A | 7/1994 | Hollister |
| 5,330,533 A | 7/1994 | Walker |
| 5,330,534 A | 7/1994 | Herrington et al. |
| 5,344,460 A | 9/1994 | Turanyi et al. |
| 5,344,461 A | 9/1994 | Phlipot |
| 5,344,494 A | 9/1994 | Davidson et al. |
| 5,358,527 A | 10/1994 | Forte |
| 5,368,881 A | 11/1994 | Kelman et al. |
| 5,370,699 A | 12/1994 | Hood et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,414,049 A | 5/1995 | Sun et al. |
| 5,449,745 A | 9/1995 | Sun et al. |
| 5,458,637 A | 10/1995 | Hayes |
| 5,480,446 A | 1/1996 | Goodfellow et al. |
| 5,543,471 A | 8/1996 | Sun et al. |
| 5,549,686 A | 8/1996 | Johnson et al. |
| 5,571,187 A | 11/1996 | Devanathan |
| 5,571,194 A | 11/1996 | Gabriel |
| 5,609,639 A | 3/1997 | Walker |
| 5,609,643 A | 3/1997 | Colleran et al. |
| 5,639,279 A | 6/1997 | Burkinshaw et al. |
| 5,650,485 A | 7/1997 | Sun et al. |
| 5,658,333 A | 8/1997 | Kelman et al. |
| 5,658,342 A | 8/1997 | Draganich et al. |
| 5,658,344 A | 8/1997 | Hurlburt |
| 5,681,354 A | 10/1997 | Eckhoff |
| 5,683,468 A | 11/1997 | Pappas |
| 5,702,458 A | 12/1997 | Burstein et al. |
| 5,702,463 A | 12/1997 | Pothier et al. |
| 5,702,464 A | 12/1997 | Lackey et al. |
| 5,702,466 A | 12/1997 | Pappas et al. |
| 5,728,748 A | 3/1998 | Sun et al. |
| 5,732,469 A | 3/1998 | Hamamoto et al. |
| 5,755,800 A | 5/1998 | O'Neil et al. |
| 5,755,801 A | 5/1998 | Walker et al. |
| 5,755,803 A | 5/1998 | Haines et al. |
| 5,765,095 A | 6/1998 | Flak et al. |
| 5,766,257 A | 6/1998 | Goodman et al. |
| 5,776,201 A | 7/1998 | Colleran et al. |
| 5,800,552 A | 9/1998 | Forte |
| 5,811,543 A | 9/1998 | Hao et al. |
| 5,824,096 A | 10/1998 | Pappas et al. |
| 5,824,100 A | 10/1998 | Kester et al. |
| 5,824,102 A | 10/1998 | Buscayret |
| 5,824,103 A | 10/1998 | Williams |
| 5,871,543 A | 2/1999 | Hofmann |
| 5,871,545 A | 2/1999 | Goodfellow et al. |
| 5,871,546 A | 2/1999 | Colleran et al. |
| 5,879,394 A | 3/1999 | Ashby et al. |
| 5,879,400 A | 3/1999 | Merrill et al. |
| 5,906,644 A | 5/1999 | Powell |
| 5,935,173 A | 8/1999 | Roger et al. |
| 5,951,603 A | 9/1999 | O'Neil et al. |
| 5,957,979 A | 9/1999 | Beckman et al. |
| 5,964,808 A | 10/1999 | Blaha et al. |
| 5,976,147 A | 11/1999 | Lasalle et al. |
| 5,984,969 A | 11/1999 | Matthews et al. |
| 5,989,027 A | 11/1999 | Wagner et al. |
| 5,997,577 A | 12/1999 | Herrington et al. |
| 6,004,351 A | 12/1999 | Tomita et al. |
| 6,005,018 A | 12/1999 | Cicierega et al. |
| 6,010,534 A | 1/2000 | O'Neil et al. |
| 6,013,103 A | 1/2000 | Kaufman et al. |
| 6,017,975 A | 1/2000 | Saum et al. |
| 6,039,764 A | 3/2000 | Pottenger et al. |
| 6,042,780 A | 3/2000 | Huang |
| 6,053,945 A | 4/2000 | O'Neil et al. |
| 6,059,949 A | 5/2000 | Gal-Or et al. |
| 6,068,658 A | 5/2000 | Insall et al. |
| 6,080,195 A | 6/2000 | Colleran et al. |
| 6,090,144 A | 7/2000 | Letot et al. |
| 6,123,728 A | 9/2000 | Brosnahan et al. |
| 6,123,729 A | 9/2000 | Insall et al. |
| 6,123,896 A | 9/2000 | Meeks et al. |
| 6,126,692 A | 10/2000 | Robie et al. |
| 6,135,857 A | 10/2000 | Shaw et al. |
| 6,139,581 A | 10/2000 | Engh et al. |
| 6,152,960 A | 11/2000 | Pappas |
| 6,162,254 A | 12/2000 | Timoteo |
| 6,174,934 B1 | 1/2001 | Sun et al. |
| 6,206,926 B1 | 3/2001 | Pappas |
| 6,210,444 B1 | 4/2001 | Webster et al. |
| 6,210,445 B1 | 4/2001 | Zawadzki |
| 6,217,618 B1 | 4/2001 | Hileman |
| 6,228,900 B1 | 5/2001 | Shen et al. |
| 6,238,434 B1 | 5/2001 | Pappas |
| 6,242,507 B1 | 6/2001 | Saum et al. |
| 6,245,276 B1 | 6/2001 | McNulty et al. |
| 6,258,127 B1 | 7/2001 | Schmotzer |
| 6,264,697 B1 | 7/2001 | Walker |

(56) References Cited

U.S. PATENT DOCUMENTS

| | | |
|---|---|---|
| 6,280,476 B1 | 8/2001 | Metzger et al. |
| 6,281,264 B1 | 8/2001 | Salovey et al. |
| 6,299,646 B1 | 10/2001 | Chambat et al. |
| 6,316,158 B1 | 11/2001 | Saum et al. |
| 6,319,283 B1 | 11/2001 | Insall et al. |
| 6,325,828 B1 | 12/2001 | Dennis et al. |
| 6,344,059 B1 | 2/2002 | Krakovits et al. |
| 6,361,564 B1 | 3/2002 | Marceaux et al. |
| 6,372,814 B1 | 4/2002 | Sun et al. |
| 6,379,388 B1 | 4/2002 | Ensign et al. |
| 6,428,577 B1 | 8/2002 | Evans et al. |
| 6,443,991 B1 | 9/2002 | Running |
| 6,475,241 B2 | 11/2002 | Pappas |
| 6,485,519 B2 | 11/2002 | Meyers et al. |
| 6,491,726 B2 | 12/2002 | Pappas |
| 6,494,914 B2 | 12/2002 | Brown et al. |
| 6,503,280 B2 | 1/2003 | Repicci |
| 6,506,215 B1 | 1/2003 | Letot et al. |
| 6,506,216 B1 | 1/2003 | McCue et al. |
| 6,524,522 B2 | 2/2003 | Vaidyanathan et al. |
| 6,540,787 B2 | 4/2003 | Biegun et al. |
| 6,558,426 B1 | 5/2003 | Masini |
| 6,569,202 B2 | 5/2003 | Whiteside |
| 6,582,469 B1 | 6/2003 | Tornier |
| 6,582,470 B1 | 6/2003 | Lee et al. |
| 6,589,283 B1 | 7/2003 | Metzger et al. |
| 6,592,787 B2 | 7/2003 | Pickrell et al. |
| 6,620,198 B2 | 9/2003 | Burstein et al. |
| 6,623,526 B1 | 9/2003 | Lloyd |
| 6,645,251 B2 | 11/2003 | Salehi et al. |
| 6,660,039 B1 | 12/2003 | Evans et al. |
| 6,660,224 B2 | 12/2003 | Lefebvre et al. |
| 6,664,308 B2 | 12/2003 | Sun et al. |
| 6,702,821 B2 | 3/2004 | Bonutti |
| 6,719,800 B2 | 4/2004 | Meyers et al. |
| 6,726,724 B2 | 4/2004 | Repicci |
| 6,730,128 B2 | 5/2004 | Burstein |
| 6,764,516 B2 | 7/2004 | Pappas |
| 6,770,078 B2 | 8/2004 | Bonutti |
| 6,770,099 B2 | 8/2004 | Andriacchi et al. |
| 6,773,461 B2 | 8/2004 | Meyers et al. |
| 6,797,005 B2 | 9/2004 | Pappas |
| 6,818,020 B2 | 11/2004 | Sun et al. |
| 6,846,327 B2 | 1/2005 | Khandkar et al. |
| 6,846,329 B2 | 1/2005 | McMinn |
| 6,849,230 B1 | 2/2005 | Feichtinger |
| 6,852,272 B2 | 2/2005 | Artz et al. |
| 6,869,448 B2 | 3/2005 | Tuke et al. |
| 6,893,388 B2 | 5/2005 | Reising et al. |
| 6,893,467 B1 | 5/2005 | Bercovy |
| 6,916,340 B2 | 7/2005 | Metzger et al. |
| 6,923,832 B1 | 8/2005 | Sharkey et al. |
| 6,926,738 B2 | 8/2005 | Wyss |
| 6,942,670 B2 | 9/2005 | Heldreth et al. |
| 6,972,039 B2 | 12/2005 | Metzger et al. |
| 6,986,791 B1 | 1/2006 | Metzger |
| 7,025,788 B2 | 4/2006 | Metzger et al. |
| 7,048,741 B2 | 5/2006 | Swanson |
| 7,066,963 B2 | 6/2006 | Naegerl |
| 7,070,622 B1 | 7/2006 | Brown et al. |
| 7,081,137 B1 | 7/2006 | Servidio |
| 7,094,259 B2 | 8/2006 | Tarabichi |
| 7,101,401 B2 | 9/2006 | Brack |
| 7,104,996 B2 | 9/2006 | Bonutti |
| 7,105,027 B2 | 9/2006 | Lipman et al. |
| 7,147,819 B2 | 12/2006 | Bram et al. |
| 7,160,330 B2 | 1/2007 | Axelson, Jr. et al. |
| 7,175,665 B2 | 2/2007 | German et al. |
| 7,255,715 B2 | 8/2007 | Metzger |
| 7,261,740 B2 | 8/2007 | Tuttle et al. |
| 7,297,164 B2 | 11/2007 | Johnson et al. |
| 7,326,252 B2 | 2/2008 | Otto et al. |
| 7,341,602 B2 | 3/2008 | Fell et al. |
| 7,344,460 B2 | 3/2008 | Gait |
| 7,357,817 B2 | 4/2008 | D'Alessio, II |
| 7,422,605 B2 | 9/2008 | Burstein et al. |
| 7,510,557 B1 | 3/2009 | Bonutti |
| 7,527,650 B2 | 5/2009 | Johnson et al. |
| 7,572,292 B2 | 8/2009 | Crabtree et al. |
| 7,578,850 B2 | 8/2009 | Kuczynski et al. |
| 7,608,079 B1 | 10/2009 | Blackwell et al. |
| 7,611,519 B2 | 11/2009 | Lefevre et al. |
| 7,615,054 B1 | 11/2009 | Bonutti |
| 7,618,462 B2 | 11/2009 | Ek |
| 7,628,818 B2 | 12/2009 | Hazebrouck et al. |
| 7,635,390 B1 | 12/2009 | Bonutti |
| 7,658,767 B2 | 2/2010 | Wyss |
| 7,678,151 B2 | 3/2010 | Ek |
| 7,678,152 B2 | 3/2010 | Suguro et al. |
| 7,708,740 B1 | 5/2010 | Bonutti |
| 7,708,741 B1 | 5/2010 | Bonutti |
| 7,740,662 B2 | 6/2010 | Barnett et al. |
| 7,749,229 B1 | 7/2010 | Bonutti |
| 7,753,960 B2 | 7/2010 | Cipolletti et al. |
| 7,771,484 B2 | 8/2010 | Campbell |
| 7,776,044 B2 | 8/2010 | Pendleton et al. |
| 7,806,896 B1 | 10/2010 | Bonutti |
| 7,806,897 B1 | 10/2010 | Bonutti |
| 7,837,736 B2 | 11/2010 | Bonutti |
| 7,842,093 B2 | 11/2010 | Peters et al. |
| 7,875,081 B2 | 1/2011 | Lipman et al. |
| 7,922,771 B2 | 4/2011 | Otto et al. |
| 8,187,335 B2 | 5/2012 | Wyss et al. |
| 8,192,498 B2 | 6/2012 | Wagner et al. |
| 8,206,451 B2 | 6/2012 | Wyss et al. |
| 8,236,061 B2 | 8/2012 | Heldreth et al. |
| 8,795,380 B2 | 8/2014 | Heldreth et al. |
| 9,539,099 B2 | 1/2017 | Heldreth et al. |
| 2002/0138150 A1 | 9/2002 | Leclercq |
| 2003/0009232 A1 | 1/2003 | Metzger et al. |
| 2003/0035747 A1 | 2/2003 | Anderson et al. |
| 2003/0044301 A1 | 3/2003 | Lefebvre et al. |
| 2003/0075013 A1 | 4/2003 | Grohowski |
| 2003/0139817 A1 | 7/2003 | Tuke et al. |
| 2003/0153981 A1 | 8/2003 | Wang et al. |
| 2003/0171820 A1 | 9/2003 | Wilshaw et al. |
| 2003/0199985 A1 | 10/2003 | Masini |
| 2003/0212161 A1 | 11/2003 | McKellop et al. |
| 2003/0225456 A1 | 12/2003 | Ek |
| 2004/0015770 A1 | 1/2004 | Kimoto |
| 2004/0039450 A1 | 2/2004 | Griner et al. |
| 2004/0167633 A1 | 8/2004 | Wen et al. |
| 2004/0186583 A1 | 9/2004 | Keller |
| 2004/0215345 A1 | 10/2004 | Perrone, Jr. et al. |
| 2004/0243244 A1 | 12/2004 | Otto et al. |
| 2004/0243245 A1 | 12/2004 | Plumet et al. |
| 2005/0021147 A1 | 1/2005 | Tarabichi |
| 2005/0055102 A1 | 3/2005 | Tornier et al. |
| 2005/0059750 A1 | 3/2005 | Sun et al. |
| 2005/0069629 A1 | 3/2005 | Becker et al. |
| 2005/0096747 A1 | 5/2005 | Tuttle et al. |
| 2005/0100578 A1 | 5/2005 | Schmid et al. |
| 2005/0123672 A1 | 6/2005 | Justin et al. |
| 2005/0143832 A1 | 6/2005 | Carson |
| 2005/0154472 A1 | 7/2005 | Afriat |
| 2005/0203631 A1 | 9/2005 | Daniels et al. |
| 2005/0209701 A1 | 9/2005 | Suguro et al. |
| 2005/0209702 A1 | 9/2005 | Todd et al. |
| 2005/0249625 A1 | 11/2005 | Brain et al. |
| 2005/0278035 A1 | 12/2005 | Wyss et al. |
| 2006/0002810 A1 | 1/2006 | Grohowski |
| 2006/0015185 A1 | 1/2006 | Chambat et al. |
| 2006/0036329 A1 | 2/2006 | Webster et al. |
| 2006/0052875 A1 | 3/2006 | Bernero et al. |
| 2006/0100714 A1 | 5/2006 | Ensign |
| 2006/0178749 A1 | 8/2006 | Pendleton et al. |
| 2006/0195195 A1 | 8/2006 | Burstein et al. |
| 2006/0228247 A1 | 10/2006 | Grohowski |
| 2006/0231402 A1 | 10/2006 | Clasen et al. |
| 2006/0241781 A1 | 10/2006 | Brown et al. |
| 2006/0257358 A1 | 11/2006 | Wen et al. |
| 2006/0271191 A1 | 11/2006 | Hermansson |
| 2006/0289388 A1 | 12/2006 | Yang et al. |
| 2007/0061014 A1 | 3/2007 | Naegerl |

(56) References Cited

U.S. PATENT DOCUMENTS

| | | |
|---|---|---|
| 2007/0073409 A1 | 3/2007 | Cooney et al. |
| 2007/0078521 A1 | 4/2007 | Overholser et al. |
| 2007/0100463 A1 | 5/2007 | Aram et al. |
| 2007/0129809 A1 | 6/2007 | Meridew et al. |
| 2007/0135926 A1 | 6/2007 | Walker |
| 2007/0173948 A1 | 7/2007 | Meridew et al. |
| 2007/0196230 A1 | 8/2007 | Hamman et al. |
| 2007/0203582 A1 | 8/2007 | Campbell |
| 2007/0219639 A1 | 9/2007 | Otto et al. |
| 2007/0293647 A1 | 12/2007 | McKellop et al. |
| 2008/0004708 A1 | 1/2008 | Wyss |
| 2008/0021566 A1 | 1/2008 | Peters et al. |
| 2008/0091272 A1 | 4/2008 | Aram et al. |
| 2008/0097616 A1 | 4/2008 | Meyers et al. |
| 2008/0114462 A1 | 5/2008 | Guidera et al. |
| 2008/0114464 A1 | 5/2008 | Barnett et al. |
| 2008/0119940 A1 | 5/2008 | Otto et al. |
| 2008/0161927 A1 | 7/2008 | Savage et al. |
| 2008/0195108 A1 | 8/2008 | Bhatnagar et al. |
| 2008/0199720 A1 | 8/2008 | Liu |
| 2008/0206297 A1 | 8/2008 | Roeder et al. |
| 2008/0269596 A1 | 10/2008 | Revie et al. |
| 2009/0043396 A1 | 2/2009 | Komistek |
| 2009/0048680 A1 | 2/2009 | Naegerl |
| 2009/0082873 A1 | 3/2009 | Hazebrouck et al. |
| 2009/0084491 A1 | 4/2009 | Uthgenannt et al. |
| 2009/0088859 A1 | 4/2009 | Hazebrouck et al. |
| 2009/0125114 A1 | 5/2009 | May et al. |
| 2009/0192610 A1 | 7/2009 | Case et al. |
| 2009/0265012 A1 | 10/2009 | Engh et al. |
| 2009/0265013 A1 | 10/2009 | Mandell |
| 2009/0292365 A1 | 11/2009 | Smith et al. |
| 2009/0295035 A1 | 12/2009 | Evans |
| 2009/0306785 A1 | 12/2009 | Farrar et al. |
| 2009/0319047 A1 | 12/2009 | Walker |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2009/0326674 A1 | 12/2009 | Liu et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0042224 A1 | 2/2010 | Otto et al. |
| 2010/0042225 A1 | 2/2010 | Shur |
| 2010/0063594 A1 | 3/2010 | Hazebrouck et al. |
| 2010/0070045 A1 | 3/2010 | Ek |
| 2010/0076563 A1 | 3/2010 | Otto et al. |
| 2010/0076564 A1 | 3/2010 | Schilling et al. |
| 2010/0094429 A1 | 4/2010 | Otto |
| 2010/0098574 A1 | 4/2010 | Liu et al. |
| 2010/0100189 A1 | 4/2010 | Metzger |
| 2010/0100190 A1 | 4/2010 | May et al. |
| 2010/0100191 A1 | 4/2010 | May et al. |
| 2010/0125337 A1 | 5/2010 | Grecco et al. |
| 2010/0161067 A1 | 6/2010 | Saleh et al. |
| 2010/0191341 A1 | 7/2010 | Byrd |
| 2010/0222890 A1 | 9/2010 | Barnett et al. |
| 2010/0286788 A1 | 11/2010 | Komistek |
| 2010/0292804 A1 | 11/2010 | Samuelson |
| 2010/0305710 A1 | 12/2010 | Metzger et al. |
| 2010/0312350 A1 | 12/2010 | Bonutti |
| 2011/0029090 A1 | 2/2011 | Zannis et al. |
| 2011/0029092 A1 | 2/2011 | Deruntz et al. |
| 2011/0035017 A1 | 2/2011 | Deffenbaugh et al. |
| 2011/0035018 A1 | 2/2011 | Deffenbaugh et al. |
| 2011/0106268 A1 | 5/2011 | Deffenbaugh et al. |
| 2011/0118847 A1 | 5/2011 | Lipman et al. |
| 2011/0125280 A1 | 5/2011 | Otto et al. |
| 2011/0153026 A1 | 6/2011 | Heggendorn et al. |
| 2012/0239158 A1 | 9/2012 | Wagner et al. |
| 2012/0259417 A1 | 10/2012 | Wyss et al. |
| 2012/0296437 A1 | 11/2012 | Wyss et al. |
| 2013/0006372 A1 | 1/2013 | Wyss et al. |
| 2013/0006373 A1 | 1/2013 | Wyss et al. |

FOREIGN PATENT DOCUMENTS

| | | |
|---|---|---|
| DE | 4308563 A1 | 9/1994 |
| DE | 19529824 A1 | 2/1997 |
| EP | 495340 A1 | 7/1992 |
| EP | 510178 A1 | 10/1992 |
| EP | 634155 A2 | 1/1995 |
| EP | 634156 A2 | 1/1995 |
| EP | 636352 A2 | 2/1995 |
| EP | 0636352 A2 | 2/1995 |
| EP | 732091 A2 | 9/1996 |
| EP | 732092 A2 | 9/1996 |
| EP | 765645 A2 | 4/1997 |
| EP | 883388 A1 | 12/1998 |
| EP | 1129676 A1 | 9/2001 |
| EP | 1196118 A1 | 4/2002 |
| EP | 1226799 A1 | 7/2002 |
| EP | 1374805 A2 | 1/2004 |
| EP | 1421918 A1 | 5/2004 |
| EP | 1440675 A1 | 7/2004 |
| EP | 1470801 A1 | 10/2004 |
| EP | 1518521 A2 | 3/2005 |
| EP | 1591082 A2 | 11/2005 |
| EP | 1779812 A1 | 5/2007 |
| EP | 1923079 A1 | 5/2008 |
| FR | 2417971 A1 | 9/1979 |
| FR | 2621243 A1 | 4/1989 |
| FR | 2653992 A1 | 5/1991 |
| FR | 2780636 A1 | 1/2000 |
| FR | 2787012 A1 | 6/2000 |
| FR | 2809302 A1 | 11/2001 |
| FR | 2835178 A1 | 8/2003 |
| GB | 1065354 A | 4/1967 |
| GB | 2293109 A | 3/1996 |
| GB | 2335145 A | 9/1999 |
| JP | 62205201 A | 9/1987 |
| JP | H08500992 A | 2/1996 |
| JP | H08224263 A | 9/1996 |
| JP | 2002291779 A | 10/2002 |
| JP | 2004167255 A | 6/2004 |
| JP | 2006015133 A | 1/2006 |
| JP | 2009501393 A | 1/2009 |
| WO | 7900739 A1 | 10/1979 |
| WO | 8100784 A1 | 3/1981 |
| WO | 8906947 A1 | 8/1989 |
| WO | 9014806 A1 | 12/1990 |
| WO | 9601725 A1 | 1/1996 |
| WO | 9623458 A1 | 8/1996 |
| WO | 9624311 A1 | 8/1996 |
| WO | 9624312 A1 | 8/1996 |
| WO | 9846171 A1 | 10/1998 |
| WO | 9927872 A1 | 6/1999 |
| WO | 0209624 A1 | 12/1999 |
| WO | 9966864 A1 | 12/1999 |
| WO | 03039609 A1 | 5/2003 |
| WO | 03101647 A1 | 12/2003 |
| WO | 2004058108 A1 | 7/2004 |
| WO | 2004069104 A1 | 8/2004 |
| WO | 05009489 A2 | 2/2005 |
| WO | 05009729 A2 | 2/2005 |
| WO | 2005072657 A1 | 8/2005 |
| WO | 2005087125 A2 | 9/2005 |
| WO | 06014294 A1 | 2/2006 |
| WO | 06130350 A2 | 12/2006 |
| WO | 2007106172 A1 | 9/2007 |
| WO | 2007108804 A1 | 9/2007 |
| WO | 2007119173 A2 | 10/2007 |
| WO | 09046212 | 4/2009 |
| WO | 09128943 | 10/2009 |

OTHER PUBLICATIONS

Zimmer Nexgen Trabecular Metal Tibial Tray, The Best Thing Next to Bone, 97-5954-001-00, 2007, 4 pages.

(56) References Cited

OTHER PUBLICATIONS

European Search Report for European Patent Application No. 08253140.1-2310, dated Dec. 23, 2008, 7 pgs.
Koo, et al., "The Knee Joint Center of Rotation Is Predominantly on the Lateral Side During Normal Walking", Journal of Biomechanics, vol. 41 (2008): 1269-1273, 5 Pages.
"NexGen Complete Knee Solution Cruciate Retaining Knee (CR)," Zimmer, available at: http://zimmer.com.au/ctl?template=PC&op=global&action=&template=PC&id=356- , downloaded on Feb. 18, 2009, (1 page).
"Vanguard Complete Knee System," Biomet, available at: http://www.biomet.com/patients/vanguard_complete.cfm, downloaded on Feb. 2009, (3 pages).
Biomet, Vanguard Mono-Lock Tibial System, Patented Convertible Tibial Bearing Technology, 2009, 2 Pages.
European Patent Office, Search Report for App. No. 09164479.9-2310, dated Nov. 4, 2009, 6 pages.
European Search Report for European Patent Application No. 08164944.4-2310-2042131, dated Mar. 16, 2009, 12 pgs.
European Search Report for European Patent Application No. 09164235.5-1526, dated Dec. 22, 2009, 6 pgs.
European Search Report for European Patent Application No. 09164245.4-2310, dated Oct. 15, 2009, 5 pgs.
European Search Report by for European Patent Application No. 09164478.1-2310, dated Oct. 20, 2009, 6 Pages.
Japanese Search Report for Japanese Patent Application No. 2009-501393, dated Oct. 26, 2010, 5 Pages.
Karachalios, et al., "A Mid-Term Clinical Outcome Study of the Advance Medial Pivot Knee Arthroplasty", www.sciencedirect.come, The Knee 16 (2009); 484-488, 5 Pages.
Mannan, et al., "The Medical Rotation Total Knee Replacement: A Clinical and Radiological Review at a Mean Follow-Up of Six Years", The Journal of Bone and Joint Surgery, vol. 91-B, No. 6 (Jun. 2009): 750-756, 7 Pages.
Moonot, et al., "Correlation Between the Oxford Knee and American Knee Society Scores at Mid-Term Follow-Up", The Journal of Knee Surgery, vol. 22, No. 3 (Jul. 2009), 226-230, 5 Page.
Omori, et al., "The Effect of Geometry of the Tibial Polyethylene Insert on the Tibiofemoral Contact Kinematics in Advance Medical Pivot Total Knee Arthroplasty", The Journal of Orthopaedics Science (2009), 14:754-760, 7 Pages.
Zimmer, Trabecular Metal Monoblock Tibial Components, An Optimal Combination of Material and Design, www.zimmer.com, 2009, 3 pages.
Barnes, C.L., et al., "Kneeling Is Safe for Patients Implanted With Medical-Pivot Total Knee Arthoplasty Designs, Journal of Arthoplasty", vol. 00, No. 0 2010, 1-6, 6 Pages.
Depuy Orthopaedics, Inc., "Sigma Fixed Bearing Knees—Function with Wear Resistance", 2010, 0612-65-508 (Rev. 1) 20 pages.
European Search Report for European Patent Application No. 06739287.8-2310, dated Mar. 16, 2010, 3 Pages.
European Search Report for European Patent Application No. 09164160.5-1526, dated Jan. 4, 2010, 4 pgs.
European Search Report for European Patent Application No. 09164168.8-1526, dated Jan. 4, 2010, 6 pgs.
European Search Report for European Patent Application No. 09164228.0-1526, dated Feb. 2, 2010, 6 pgs.
European Search Report for European Patent Application No. 09164478.1-2310, dated Apr. 28, 2010, 12 Pages.
European Search Report for European Patent Application No. 10162138.1, dated Aug. 30, 2010, 7 Pages.
European Search Report, European Application No. 10174439.9-1526, dated Dec. 20, 2010, 4 pages.
Fan, Cheng-Yu, et al., "Primitive Results After Medical-Pivot Knee Arthroplasties: A Minimum 5 Year Follow-Up Study", The Journal of Arthroplasty, vol. 25, No. 3 2010, 492-496, 5 Pages.
Depuy Knees International, "Sigma CR Porocoat.RTM.," 1 page, (downloaded May 12, 2011).
European Search Report for European Patent Application No. 11150648.1-2310, dated Apr. 7, 2011, 4 pages.

European Search Report for European Patent Application No. 11150648.1-2310, dated Apr. 7, 2011, 5 Pgs.
State Intellectual Property Office of People's Republic China; Chinese Search Report; Application No. 200910166935.6; dated Mar. 26, 2013; 2 pages.
Dennis et al., Multicenter Determination of In Vivo Kinematics After Total Knee Arthroplasty, "Clin. Orthop. Rel. Res., 416, 37-57, 21 pgs."
PEEK-OPTIMA.RTM., The Polymer for Implants, Technical Information for the Medical Professional ", 7 pages."
Operative Technique, Johnson Elloy Knee System, Chas F. Thackray, Ltd., 1988, 34 pgs.
Effects of Coronal Plane Conformity on Tibial Loading in TKA: A Comparison of AGC Flat Versus Conforming Articulations, Brent, et al, Orthopaedic Surgery, Surgical Technology International, XVIII, 6 pages.
Scorpio Knee TS Single Axis Revision Knee System, Stryker Orthopaedics, http://www.stryker.com/stellent/groups/public/documents/web_prod/023609.p- df, (6 pages).
Shaw et al., "The Longitudinal Axis of the Knee and the Role of the Cruciate Ligaments in Controlling Transverse Rotation", J.Bone Joint Surg. Am. 1974:56:1603-1609, 8 Pages.
Goodfellow et al., "The Mechanics of the Knee and Prosthesis Design," The Journal of Bone and Joint Surgery, vol. 60-B, No. 3, Aug. 1978, 12 pgs.
Clary et al., "Kinematics of Posterior Stabilized and Cruciate Retaining Knee Implants During an in Vitro Deep Knee Bend," 54th Annual Meeting of the Orthopaedic Research Society, Poster No. 1983, Mar. 2008.
Kurosawa, et al., "Geometry and Motion of the Knee for Implant and Orthotic Design", The Journal of Biomechanics 18 (1985), pp. 487-499, 12 Pages.
2nd Int'l Johnson-Elloy Knee Meeting, Mar. 1987, 9 pages.
Prosthesis and Instrumentation the Turning Point, Accord, The Johnson/Elloy Concept, Chas F. Thackray Ltd, 8 pages (1988).
Murphy, Michael Charles, "Geometry and the Kinematics of the Normal Human Knee", Submitted to Masachusetts Institute of Technology (1990), 379 Pages.
The Accuracy of Intramedullary Alignment in Total Knee Replacement, Elloy, et al, Chas F. Thackray Ltd, 12 pages (1992).
Factors Affecting the Range of Movement of Total Knee Arthroplasty, Harvey et al, The Journal of Bone and Joint Surgery, vol. 75-B, No. 6, Nov. 1993, 6 pages.
Five to Eight Year Results of the Johnson/Elloy (Accord) Total Knee Arthroplasty, Johnson et al, The Journal of Arthroplasty, vol. 8, No. 1, Feb. 1993, 6 pages.
Depuy Inc., "AMK Total Knee System Product Brochure", 1996, 8 pages.
Fuller, et al., "A Comparison of Lower-Extremity Skeletal Kinematics Measured Using Skin and Pin-Mounted Markers", Human Movement Science 16 (1997) 219-242, 24 Pages.
Dennis et al., "In vivo anteroposterior femorotibial translation of total knee arthroplasty: a multicenter analysis," Clin Orthop Rel Res, 356: 47-57, 1998.
Depuy Orthopaedics, Inc., "AMK Total Knee System Legent II Surgical Techinque", 1998, 30 pages.
Operative Technique the Turning Point, Accord, The Johnson/Elloy Concept, Chas FL Thackray Ltd, 32 pages (1998).
Procedure, References Guide for Use with P.F.C. Sigma Knee Systems, 1998, 8 pages.
Restoration of Soft Tissue Stability, Johnson, et al., Chas. F. Thackray, Ltd., 21 pages (1998).
The Turning Point, Accord, The Johnson Elloy Concept, Chas F. Thackray Ltd, 20 pages (1998).
Depuy PFC Sigma RP, "PFC Sigma Knee System with Rotating Platform Technical Monograph", 1999, 0611-29-050 (Rev. 3), 70 pages.
Midvatus Approach in Total Knee Arthroplasty, A Description and a Cadaveric Study Determining the Distance of the Popliteal Artery From the Patellar Margin of the Incision, Cooper et al., The Journal of Arthoplasty, vol. 14 No. 4, 1999, 4 Pages.
Advice Notice (NI) Mar. 2000, Defect & Investigation Centre, Mar. 13, 2000, 3 pages.

(56) References Cited

OTHER PUBLICATIONS

Ferris, "Matching observed spiral form curves to equations of spirals in 2-D images," The First Japanese-Australian Joint Seminar, Mar. 2000, 7 pgs.
Hill, et al., "Tibiofemoral Movement 2: The Loaded and Unloaded Living Knee Studied by MRI" The Journal of Bone & Joint Surgery, vol. 82-B, No. 8 (Nov. 2000), 1196-1198, 3 Pages.
Nakagawa, et al., "Tibiofemoral Movement 3: Full Flexion of the Normal Human Knee", J.Bone Joint Surg. Am, vol. 82-B, No. 8 (2000). 1199-1200, 2 Pages.
The Effects of Conformity and Load in Total Knee Replacement, Kuster, et al, Clinical Orthopaedics and Related Research No. 375, Jun. 2000, 11 pages.
Uvehammer et al., "In vivo kinematics of total knee arthroplasty: flat compared with concave tibial joint surface," J Orthop Res 18(6): 856-64, 2000.
Asano et al. "In Vivo Three-Dimensional Knee Kinematics Using a Biplanar Image-Matching Technique," Clin Orthop Rel Res, 388: 157-166, 2001, (10 pages).
D'Lima et al., "Quadriceps moment arm and quadriceps forces after total knee arthroplasty," Clin Orthop Rel Res 393:213-20, 2001.
Bertin et al., "In Vivo Determination of Posterior Femoral Rollback for Subjects Having a NexGen Posterior Cruciate-Retaining Total Knee Arthroplasty," J. Arthroplasty, vol. 17, No. 8, 2002, 9 pgs.
The Johnson Elloy (Accord) Total Knee Replacement, Norton et al, The Journal of Bone and Joint Surgery (BR), vol. 84, No. 6, Aug. 2002, 4 pages.
Walker, et al., "Motion of a Mobile Bearing Knee Allowing Translation of Rotation", Journal of Arthroplasty 17 (2002): 11-19, 9 Pages.
Andriacchi, T.P., "The Effect of Knee Kinematics, Gait and Wear on the Short and Long-Term Outcomes of Primary Knee Replacement," NIH Consensus Development Conference on Total Knee Replacement, pp. 61-62, Dec. 8-10, 2003, (4 pages).
Blaha, et al., "Kinematics of the Human Knee Using an Open Chain Cadaver Model", Clinical Orthopaedics and Related Research, vol. 410 (2003); 25-34, 10 Pages.
Komistek, et al., "In Vivo Flouroscopic Analysis of the Normal Human Knee", Clinical Orthopaedics 410 (2003): 69-81, 13 Pages.
Ranawat, "Design may be counterproductive for optimizing flexion after TKR," Clin Orthop Rel Res 416: 174-6, 2003.
Dennis, et al. "A Multi-Center Analysis of Axial Femorotibial Rotation After Total Knee Arthoplasty", Clinical Orthopaedics 428 (2004); 180-189, 10 Pages.
Komistek, et al., "In Vivo Polyethylene Bearing Mobility Is Maintained in Posterior Stabilized Total Knee Arthroplasty", Clinical Orthopaedics 428 (2004): 207-213, 7 Pages.
Saari et al., "The effect of tibial insert design on rising from a chair; motion analysis after total knee replacement," Clin Biomech 19(9): 951-6, 2004.
Cari Zeiss, Zeiss Surfcomm 5000—"Contour and Surface Measuring Machines", 2005, 16 pages.
Dennis et al., "In Vivo Determination of Normal and Anterior Cruciate Ligament-Deficient Knee Kinematics," J. Biomechanics, 38, 241-253, 2005, 13 pgs.
Freeman, M.A.R., et al., "The Movement of the Normal Tibio-Femoral Joint", The Journal of Biomechanics 38 (2005) (2), pp. 197-208, 12 Pgs.
P. Johal et al., "Tibio-femoral movement in the living knee. A study of weight bearing and non-weight bearing knee kinematics using 'interventional' MRI," Journal of Biomechanics, vol. 38, Issue 2, Feb. 2005, pp. 269-276, (8 pages).
Wang et al., "A biomechanical comparison between the single-axis and multi-axis total knee arthroplasty systems for stand-to-sit movement," Clin Biomech 20(4): 428-33, 2005.
Yoshiya et al., "In Vivo Kinematic Comparison of Posterior Cruciate-Retaining and Posterior Stabilized Total Knee Arthroplasties Under Passive and Weight-bearing Conditions," J. Arthroplasty, vol. 20, No. 6, 2005, 7 pgs.
Li et al., "Anterior Cruciate Ligament Deficiency Alters the In Vivo Motion of the Tibiofemoral Cartilage Contact Points In Both Anteroposterior and Mediolateral Directions," JBJS-Am, vol. 88, No. 8, Aug. 2006, 10 pgs.
PCT Notification Concerning Transmittal of International Prel. Report for Corresponding International App. No. PCT/US2006/010431, dated Jun. 5, 2007, 89 Pages.
Shakespeare, et al., "Flexion After Total Knee Replacement. A Comparison Between the Medical Pivot Knee and a Posterior Stabilised Knee", www.sciencedirect.com, The Knee 13 (2006): 371-372, 3 Pages.
Suggs et al., "Three-Dimensional Tibiofemoral Articular Contact Kinematics of a Cruciate-Retaining Total Knee Arthroplasty," JBJS-Am, vol. 88, No. 2, 2006, 10 pgs.
Wang et al., "Biomechanical differences exhibited during sit-to-stand between total knee arthroplasty designs of varying radii," J Arthroplasty 21(8): 1196-9, 2006.
Kessler et al., "Sagittal curvature of total knee replacements predicts in vivo kinematics," Clinical Biomechanics 22(1): 52-58, 2007.

ORTHOPAEDIC KNEE PROSTHESIS HAVING CONTROLLED CONDYLAR CURVATURE

This continuation application claims priority under 35 U.S.C. § 120 to U.S. patent application Ser. No. 15/402,513, and entitled "Orthopaedic Knee Prosthesis Having Controlled Condylar Curvature," by Mark A. Heldreth et al., which was filed on Jan. 10, 2017 and claimed priority to U.S. patent application Ser. No. 14/309,466, now U.S. Pat. No. 9,539,099, and entitled "Orthopaedic Knee Prosthesis Having Controlled Condylar Curvature," by Mark A. Heldreth et al., which was filed on Jun. 19, 2014 and claimed priority to U.S. patent application Ser. No. 13/540,177, now U.S. Pat. No. 8,795,380, and entitled "Orthopaedic Knee Prosthesis Having Controlled Condylar Curvature," by Joseph G. Wyss et al., which was filed on Jul. 2, 2012 and claimed priority to U.S. patent application Ser. No. 12/488,107, now U.S. Pat. No. 8,236,061, entitled "Orthopaedic Knee Prosthesis Having Controlled Condylar Curvature," by Joseph G. Wyss et al., which was filed on Jun. 19, 2009 and claimed priority under 35 U.S.C. § 119(e) to U.S. Provisional Patent Application Ser. No. 61/077,124 entitled "Orthopaedic Knee Prosthesis Having Controlled Condylar Curvature," by Joseph G. Wyss et al., which was filed on Jun. 30, 2008. The entirety of each of those applications is hereby incorporated by reference.

CROSS-REFERENCE TO RELATED U.S. PATENT APPLICATION

Cross-reference is also made to U.S. Utility patent application Ser. No. 12/165,579, now U.S. Pat. No. 8,828,086, entitled "Orthopaedic Femoral Component Having Controlled Condylar Curvature" by John L. Williams et al., which was filed on Jun. 30, 2008; to U.S. Utility patent application Ser. No. 12/165,574, now U.S. Pat. No. 8,192,498, entitled "Posterior Cruciate-Retaining Orthopaedic Knee Prosthesis Having Controlled Condylar Curvature" by Christel M. Wagner, which was filed on Jun. 30, 2008; to U.S. Utility patent application Ser. No. 12/165,575, now U.S. Pat. No. 8,187,335, entitled "Posterior Stabilized Orthopaedic Knee Prosthesis Having Controlled Condylar Curvature" by Joseph G. Wyss, which was filed on Jun. 30, 2008; and to U.S. Utility patent application Ser. No. 12/165,582, now U.S. Pat. No. 8,206,451, entitled "Posterior Stabilized Orthopaedic Prosthesis" by Joseph G. Wyss, which was filed on Jun. 30, 2008; the entirety of each of which is incorporated herein by reference.

TECHNICAL FIELD

The present disclosure relates generally to orthopaedic prostheses, and particularly to orthopaedic prostheses for use in knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Depending on the severity of the damage to the patient's joint, orthopaedic prostheses of varying mobility may be used. For example, the knee prosthesis may include a "fixed" tibial bearing in cases wherein it is desirable to limit the movement of the knee prosthesis, such as when significant soft tissue loss or damage is present. Alternatively, the knee prosthesis may include a "mobile" tibial bearing in cases wherein a greater degree of freedom of movement is desired. Additionally, the knee prosthesis may be a total knee prosthesis designed to replace the femoral-tibial interface of both condyles of the patient's femur or a uni-compartmental (or uni-condylar) knee prosthesis designed to replace the femoral-tibial interface of a single condyle of the patient's femur.

The type of orthopedic knee prosthesis used to replace a patient's natural knee may also depend on whether the patient's posterior cruciate ligament is retained or sacrificed (i.e., removed) during surgery. For example, if the patient's posterior cruciate ligament is damaged, diseased, and/or otherwise removed during surgery, a posterior stabilized knee prosthesis may be used to provide additional support and/or control at later degrees of flexion. Alternatively, if the posterior cruciate ligament is intact, a cruciate retaining knee prosthesis may be used.

Typical orthopaedic knee prostheses are generally designed to duplicate the natural movement of the patient's joint. As the knee is flexed and extended, the femoral and tibial components articulate and undergo combinations of relative anterior-posterior motion and relative internal-external rotation. However, the patient's surrounding soft tissue also impacts the kinematics and stability of the orthopaedic knee prosthesis throughout the joint's range of motion. That is, forces exerted on the orthopaedic components by the patient's soft tissue may cause unwanted or undesirable motion of the orthopaedic knee prosthesis. For example, the orthopaedic knee prosthesis may exhibit an amount of unnatural (paradoxical) anterior translation as the femoral component is moved through the range of flexion.

In a typical orthopaedic knee prosthesis, paradoxical anterior translation may occur at nearly any degree of flexion, but particularly at mid to late degrees of flexion. Paradoxical anterior translation can be generally defined as an abnormal relative movement of a femoral component on a tibial bearing wherein the contact "point" between the femoral component and the tibial bearing "slides" anteriorly with respect to the tibial bearing. This paradoxical anterior translation may result in loss of joint stability, accelerated wear, abnormal knee kinematics, and/or cause the patient to experience a sensation of instability during some activities.

SUMMARY

According to one aspect, an orthopaedic knee prosthesis may include a femoral component and a tibial bearing. The femoral component may have a condyle surface curved in the sagittal plane. The tibial bearing may be a bearing surface configured to articulate with the condyle surface of the femoral component. The condyle surface of the femoral component may be configured to contact the bearing surface at a first contact point on the condyle surface at a first degree of flexion less than about 30 degrees. The condyle surface of the femoral component may be also be configured to contact the bearing surface at a second contact point on the condyle surface at a second degree of flexion greater than about 45 degrees. Additionally, the condyle surface of the femoral component may be configured to contact the bearing surface at a third contact point on the condyle surface at a third degree of flexion greater than the second degree of flexion. In some embodiments, the first degree of flexion may be in the range of 0 degrees to 10 degrees, the second degree of flexion may be in the range of 60 degrees to 70 degrees, and the third degree of flexion may be in the range of 80 degrees to 110 degrees. For example, in one particular embodiment, the first degree of flexion is about 5 degrees, the second degree of flexion is about 65 degrees, and the third degree of flexion is about 90 degrees.

The condyle surface in the sagittal plane may have a first radius of curvature at the first contact point, a second radius curvature at the second contact point, and a third radius of curvature at the third contact point. In some embodiments, the third radius of curvature may be greater than the second radius of curvature by at least 0.5 millimeters. Additionally, the condyle surface in the sagittal plane between the first contact point and the second contact point may include a plurality of curved surface sections. Each curved surface section may have a different radius of curvature.

The plurality of curved surface sections may include an anterior-most curved surface section. In some embodiments, the radius of curvature of the anterior-most curved surface section may have a length greater than the radius of curvature of any other curved surface section of the plurality of curved surface sections. Additionally, in some embodiments, the length of the radius of curvature of each curved surface section posterior to the anterior-most curved surface section may be less than the length of the radius of curvature of an anteriorly-adjacent curved surface section. For example, in some embodiments, the length of the radius of curvature of each curved surface section posterior to the anterior-most curved surface section is less than the length of the radius of curvature of an anteriorly-adjacent curved surface section by a distance in the range of 0.1 millimeters to 5 millimeters, in the range of 1 millimeters to 3 millimeters, and/or about 1 millimeter.

Each of the plurality of curved surface sections may subtend a corresponding angle. In some embodiments, each angle subtended by the plurality of curved surface sections being approximately equal. In other embodiments, the angle subtended by each of the curved surface sections posterior to the anterior-most curved surface section may be less than the angle subtended by an anteriorly-adjacent curved surface section. For example, in some embodiments, the angle subtended by each of the curved surface sections posterior to the anterior-most curved surface section may be less than the angle subtended by the anteriorly-adjacent curved surface section by an amount in the range of 0.5 degrees to 5 degrees. Additionally, in other embodiments, the angle subtended by each of the curved surface sections posterior to the anterior-most curved surface section may be greater than the angle subtended by an anteriorly-adjacent curved surface section. For example, in some embodiments, the angle subtended by each of the curved surface sections posterior to the anterior-most curved surface section may be greater than the angle subtended by the anteriorly-adjacent curved surface section by an amount in the range of 0.5 degrees to 5 degrees.

According to another aspect, an orthopaedic knee prosthesis may include a femoral component and a tibial bearing. The femoral component may have a condyle surface curved in the sagittal plane. The tibial bearing may be a bearing surface configured to articulate with the condyle surface of the femoral component. The condyle surface of the femoral component may be configured to contact the bearing surface at a first contact point on the condyle surface at a first degree of flexion in the range of 0 to about 30 degrees. The condyle surface of the femoral component may be also be configured to contact the bearing surface at a second contact point on the condyle surface at a second degree of flexion in the range of 45 degrees to 90 degrees. The condyle surface in the sagittal plane between the first contact point and the second contact point may include at least five curved surface sections. Each curved surface section may have a radius of curvature having a length different from any other curved surface section.

The plurality of curved surface sections may include an anterior-most curved surface section. The radius of curvature of the anterior-most curved surface section may have a length greater than the radius of curvature of any other curved surface section of the plurality of curved surface sections. Additionally, the length of the radius of curvature of each curved surface section posterior to the anterior-most curved surface section may be less than the length of the radius of curvature of an anteriorly-adjacent curved surface section. For example, the length of the radius of curvature of each curved surface section posterior to the anterior-most curved surface section may be less than the length of the radius of curvature of an anteriorly-adjacent curved surface section by a distance in the range of 1 millimeters to 3 millimeters.

Each of the plurality of curved surface sections may subtend a corresponding angle. In some embodiments, the angle subtended by each of the curved surface sections posterior to the anterior-most curved surface section may be less than the angle subtended by an anteriorly-adjacent curved surface section. In other embodiments, the angle subtended by each of the curved surface sections posterior to the anterior-most curved surface section may be greater than the angle subtended by an anteriorly-adjacent curved surface section.

According to another aspect, an orthopaedic knee prosthesis may include a femoral component and a tibial bearing. The femoral component may have a condyle surface curved in the sagittal plane. The tibial bearing may be a bearing surface configured to articulate with the condyle surface of the femoral component. The condyle surface of the femoral component may be configured to contact the bearing surface at a first contact point on the condyle surface at a first degree of flexion in the range of 0 to about 30 degrees. The condyle surface of the femoral component may be also be configured to contact the bearing surface at a second contact point on the condyle surface at a second degree of flexion in the range of 45 degrees to 90 degrees. The condyle surface in the sagittal plane between the first contact point and the second contact point may include at least five curved surface sections. Each curved surface section may subtend a corresponding, substantially equal angle and may have a radius of curvature different from any other curved surface section.

BRIEF DESCRIPTION OF THE DRAWINGS

The detailed description particularly refers to the following figures, in which.

DETAILED DESCRIPTION OF THE DRAWINGS

Figure 1:
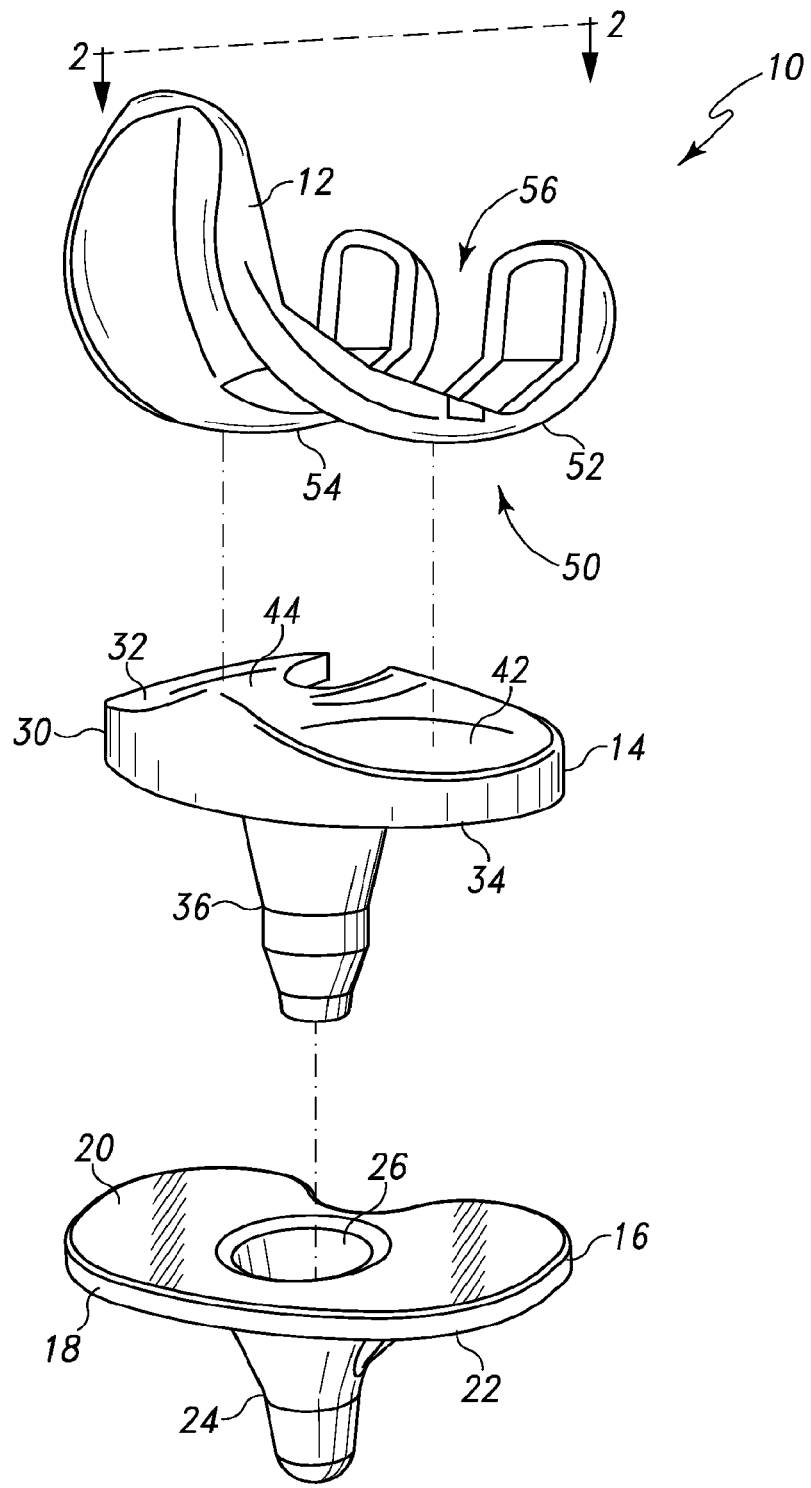
FIG. 1 is an exploded perspective view of one embodiment of an orthopaedic knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, an orthopaedic knee prosthesis 10 includes a femoral component 12, a tibial bearing 14, and a tibial tray 16. The femoral component 12 and the tibial tray 16 are illustratively formed from a metallic material such as cobalt-chromium or titanium, but may be formed from other materials, such as a ceramic material, a polymer material, a bio-engineered material, or the like, in other embodiments. The tibial bearing 14 is illustratively formed from a polymer material such as a ultra-high molecular weight polyethylene (UHMWPE), but may be formed from other materials, such as a ceramic material, a metallic material, a bio-engineered material, or the like, in other embodiments.

As discussed in more detail below, the femoral component 12 is configured to articulate with the tibial bearing 14, which is configured to be coupled with the tibial tray 16. In the illustrative embodiment of FIG. 1, the tibial bearing 14 is embodied as a rotating or mobile tibial bearing and is configured to rotate relative to the tibial tray 16 during use. However, in other embodiments, the tibial bearing 14 may be embodied as a fixed tibial bearing, which may be limited or restricted from rotating relative the tibial tray 16.

The tibial tray 16 is configured to be secured to a surgically-prepared proximal end of a patient's tibia (not shown). The tibial tray 16 may be secured to the patient's tibia via use of bone adhesive or other attachment means. The tibial tray 16 includes a platform 18 having a top surface 20 and a bottom surface 22. Illustratively, the top surface 20 is generally planar and, in some embodiments, may be highly polished. The tibial tray 16 also includes a stem 24 extending downwardly from the bottom surface 22 of the platform 18. A cavity or bore 26 is defined in the top surface 20 of the platform 18 and extends downwardly into the stem 24. The bore 26 is formed to receive a complimentary stem of the tibial insert 14 as discussed in more detail below.

As discussed above, the tibial bearing 14 is configured to be coupled with the tibial tray 16. The tibial bearing 14 includes a platform 30 having an upper bearing surface 32 and a bottom surface 34. In the illustrative embodiment wherein the tibial bearing 14 is embodied as a rotating or mobile tibial bearing, the bearing 14 includes a stem 36 extending downwardly from the bottom surface 32 of the platform 30. When the tibial bearing 14 is coupled to the tibial tray 16, the stem 36 is received in the bore 26 of the tibial tray 16. In use, the tibial bearing 14 is configured to rotate about an axis defined by the stem 36 relative to the tibial tray 16. In embodiments wherein the tibial bearing 14 is embodied as a fixed tibial bearing, the bearing 14 may or may not include the stem 22 and/or may include other devices or features to secure the tibial bearing 14 to the tibial tray 16 in a non-rotating configuration.

The upper bearing surface 32 of the tibial bearing 14 includes a medial bearing surface 42 and a lateral bearing surface 44. The medial and lateral bearing surfaces 42, 44 are configured to receive or otherwise contact corresponding medial and lateral condyles of the femoral component 12 as discussed in more detail below. As such, each of the bearing surface 42, 44 has a concave contour.

The femoral component 12 is configured to be coupled to a surgically-prepared surface of the distal end of a patient's femur (not shown). The femoral component 12 may be secured to the patient's femur via use of bone adhesive or other attachment means. The femoral component 12 includes an outer, articulating surface 50 having a pair of medial and lateral condyles 52, 54. The condyles 52, 54 are spaced apart to define an intracondyle opening 56 therebetween. In use, the condyles 52, 54 replace the natural condyles of the patient's femur and are configured to articulate on the corresponding bearing surfaces 42, 44 of the platform 30 of the tibial bearing 14.

Figure 2:
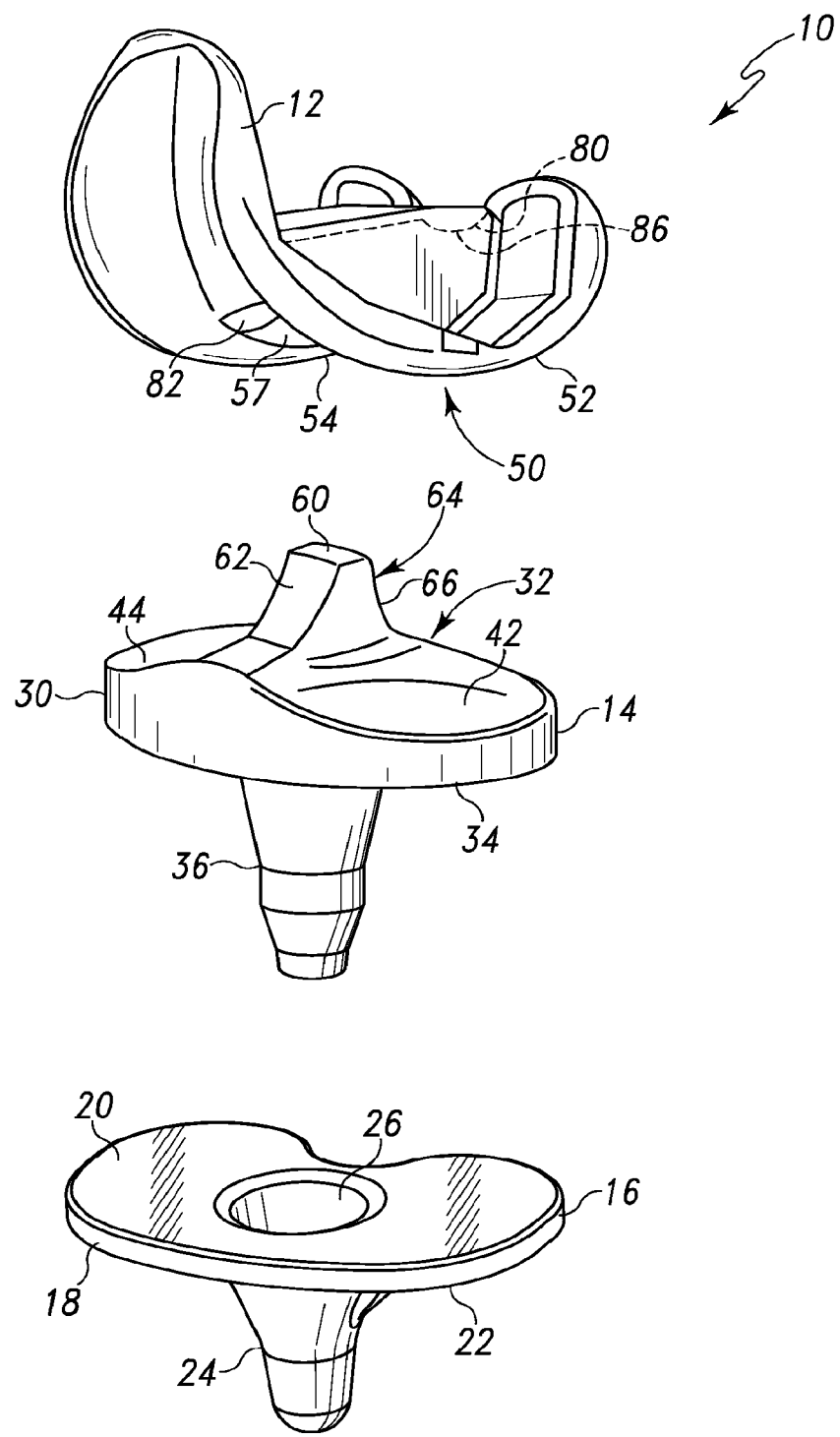
FIG. 2 is an exploded perspective view of another embodiment of an orthopaedic knee prosthesis.

The illustrative orthopaedic knee prosthesis 10 of FIG. 1 is embodied as a posterior cruciate-retaining knee prosthesis. That is, the femoral component 12 is embodied as a posterior cruciate-retaining knee prosthesis and the tibial bearing 14 is embodied as a posterior cruciate-retaining tibial bearing 14. However, in other embodiments, the orthopaedic knee prosthesis 10 may be embodied as a posterior cruciate-sacrificing knee prosthesis as illustrated in FIG. 2.

In such embodiments, the tibial bearing 14 is embodied as a posterior stabilizing tibial bearing and includes a spine 60 extending upwardly from the platform 30. The spine 60 is positioned between the bearing surfaces 42, 44 and includes an anterior side 62 and a posterior side 64 having a cam surface 66. In the illustrative embodiment, the cam surface 66 has a substantially concave curvature. However, spines 60 including cam surfaces 66 having other geometries may be used in other embodiments. For example, a tibial bearing including a spine having a substantially "S"-shaped cross-sectional profile, such as the tibial bearing described in U.S. patent application Ser. No. 12/165,582, entitled "Posterior Stabilized Orthopaedic Prosthesis" by Joseph G. Wyss, et al., which is hereby incorporated by reference, may be used in other embodiments.

Additionally, in such embodiments, the femoral component 12 is embodied as a posterior stabilized femoral component and includes an intracondyle notch or recess 57 (rather than an opening 56). A posterior cam 80 (shown in phantom) and an anterior cam 82 are positioned in the intracondyle notch 57. The posterior cam 80 is located toward the posterior side of the femoral component 12 and includes a cam surface 86 configured to engage or otherwise contact the cam surface 66 of the spine 60 of the tibial bearing 14 during flexion.

It should be appreciated that although the orthopaedic knee prosthesis 10 may be embodied as either a posterior cruciate-retaining or a cruciate-sacrificing knee prosthesis, the femoral component 12 and the tibial bearing 14 of the knee prosthesis 10 are discussed below, and illustrated in the remaining figures, in regard to a posterior cruciate-retaining knee prosthesis with the understanding that such description is equally applicable to those embodiments wherein the orthopaedic knee prosthesis 10 is embodied as a posterior cruciate-sacrificing (posterior stabilized) orthopaedic knee prosthesis.

It should be appreciated that the illustrative orthopaedic knee prosthesis 10 is configured to replace a patient's right knee and, as such, the bearing surface 42 and the condyle 52 are referred to as being medially located; and the bearing surface 44 and the condyle 54 are referred to as being laterally located. However, in other embodiments, the orthopaedic knee prosthesis 10 may be configured to replace a patient's left knee. In such embodiments, it should be appreciated that the bearing surface 42 and the condyle 52 may be laterally located and the bearing surface 44 and the condyle 54 may be medially located. Regardless, the features and concepts described herein may be incorporated in an orthopaedic knee prosthesis configured to replace either knee joint of a patient.

Figure 3:
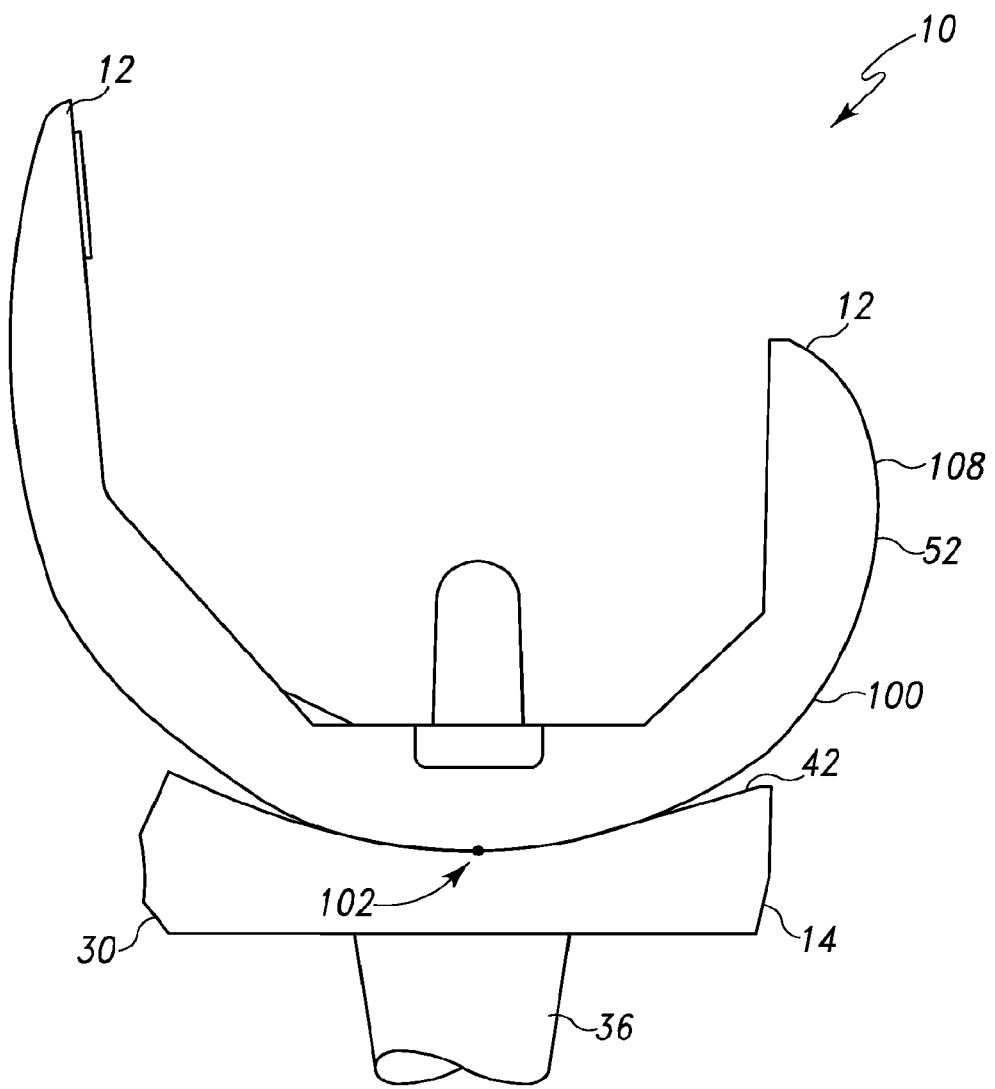
FIG. 3 is a cross-sectional view of one embodiment of a femoral component and tibial bearing of FIG. 1 taken generally along section lines 2-2 and having the femoral component articulated to a first degree of flexion.
Figure 4:
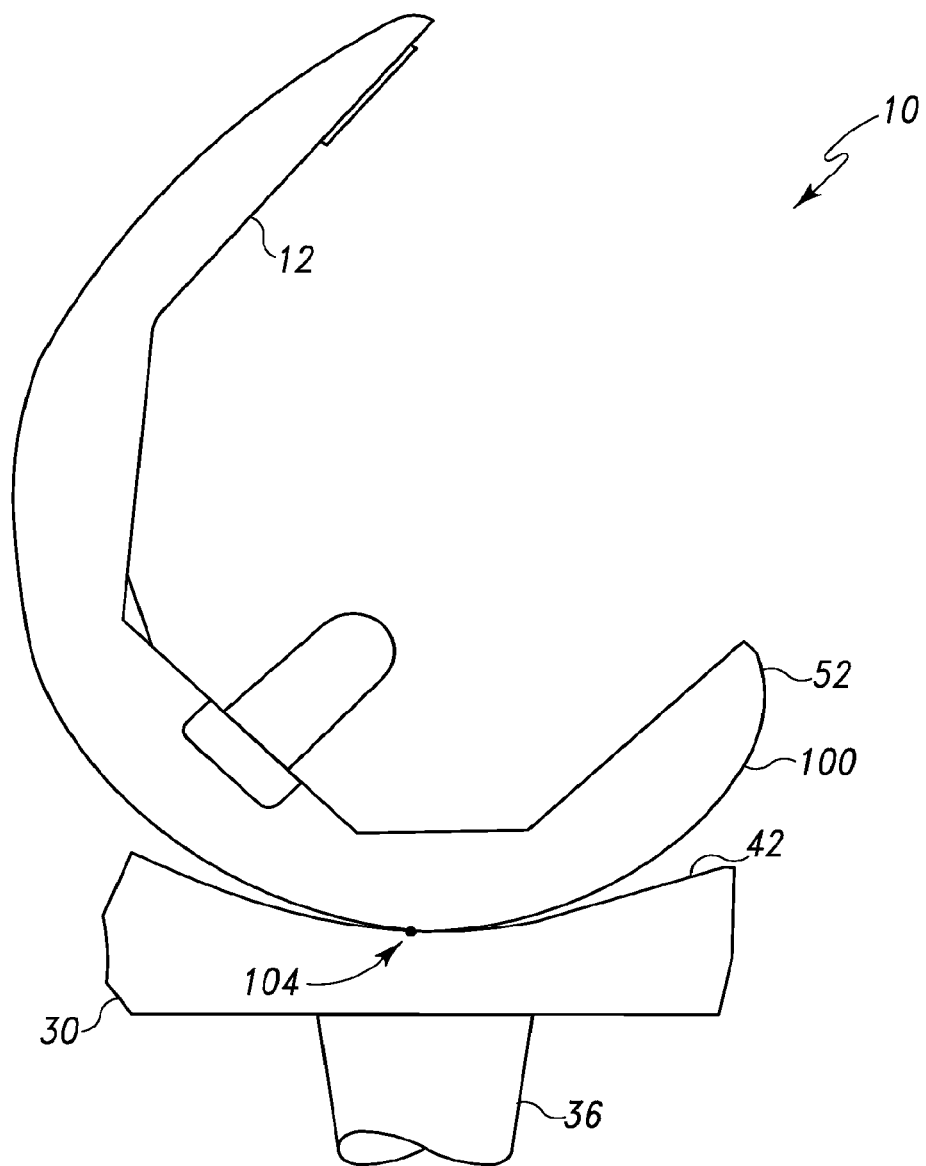
FIG. 4 is a cross-sectional view of a femoral component and tibial bearing of FIG. 3 having the femoral component articulated to a second degree of flexion.
Figure 5:
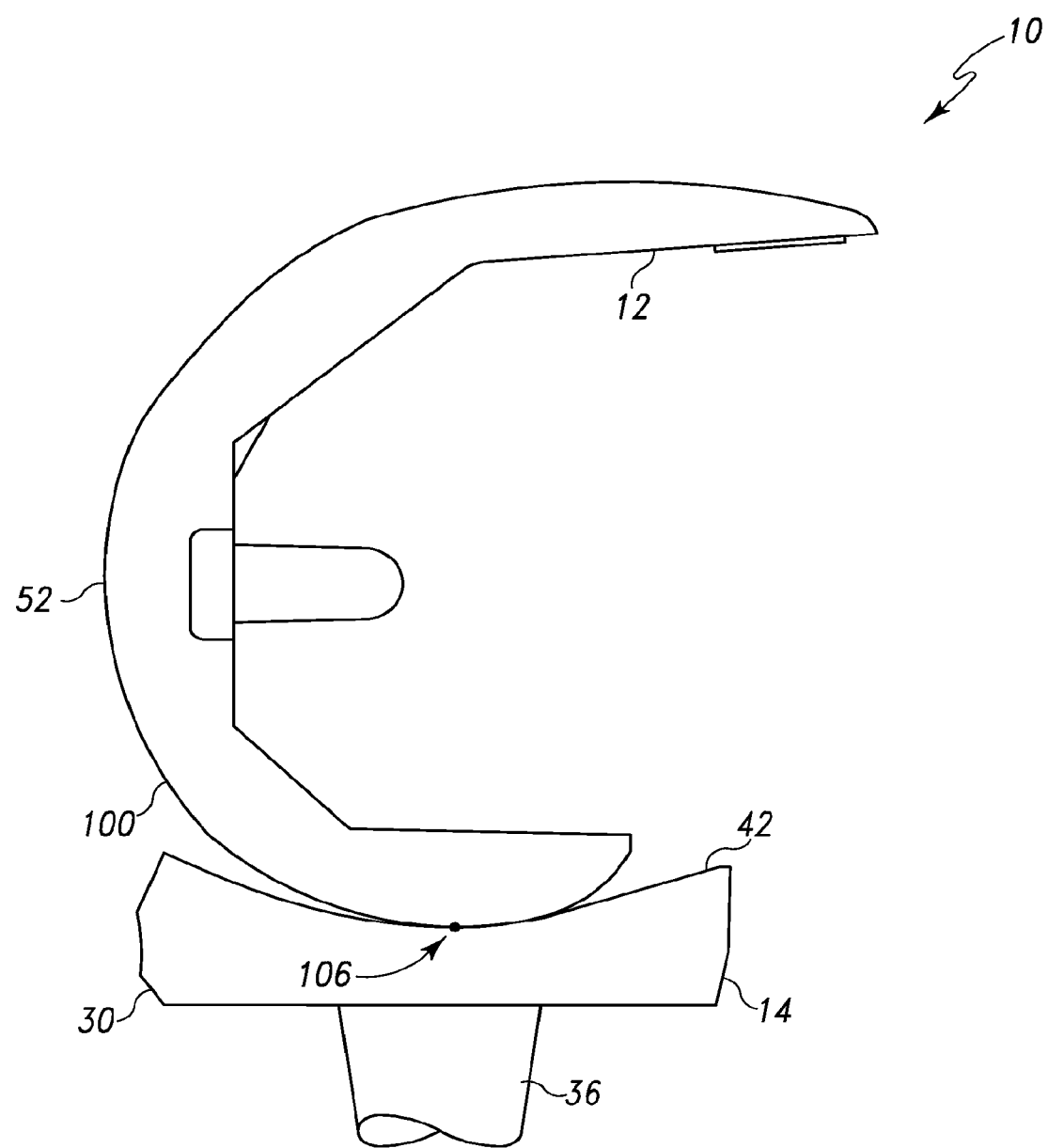
FIG. 5 is a cross-sectional view of a femoral component and tibial bearing of FIG. 3 having the femoral component articulated to a third degree of flexion.

Referring now to FIGS. 3-5, the femoral component 12 is configured to articulate on the tibial bearing 14 during use. Each condyle 52, 54 of the femoral component 12 includes a condyle surface 100, which is convexly curved in the sagittal plane and configured to contact the respective bearing surface 42, 44. For example, in one embodiment as shown in FIG. 3, when the orthopaedic knee prosthesis 10 is in extension or is otherwise not in flexion (e.g., a flexion of about 0 degrees), the condyle surface 100 of the condyle 52 contacts the bearing surface 42 (or bearing surface 44 in regard to condyle 54) at one or more contact points 102 on the condyle surface 100.

Additionally, as the orthopaedic knee prosthesis 10 is articulated through the middle degrees of flexion, the femoral component 12 contacts the tibial bearing 14 at one or more contact points on the condyle surface 100. For example, in one embodiment as illustrated in FIG. 4, when the orthopaedic knee prosthesis 10 is articulated to a middle degree of flexion (e.g., at about 45 degrees), the condyle surface 100 contacts the bearing surface 42 at one or more contact points 104 on the condyle surface 100. Similarly, as the orthopaedic knee prosthesis 10 is articulated to a late degree of flexion (e.g., at about 70 degrees of flexion), the condyle surface 100 contacts the bearing surface 42 at one or more contact points 106 on the condyle surface 100 as illustrated in FIG. 5. It should be appreciated, of course, that the femoral component 12 may contact the tibial bearing 14 at a plurality of contact points on the condyle surface 100 at any one particular degree of flexion. However, for clarity of description, only the contact points 102, 104, 106 have been illustrated in FIGS. 3-5, respectively.

The orthopaedic knee prosthesis 10 is configured such that the amount of paradoxical anterior translation of the femoral component 12 relative to the tibial bearing 14 may be reduced or otherwise delayed to a later (i.e., larger) degree of flexion. In particular, as discussed in more detail below, the condyle surface 100 of one or both of the condyles 52, 54 has particular geometry or curvature configured to reduce and/or delay anterior translations and, in some embodiments, promote "roll-back" or posterior translation, of the femoral component 12. It should be appreciated that by delaying the onset of paradoxical anterior translation of the femoral component 12 to a larger degree of flexion, the overall occurrence of paradoxical anterior translation may be reduced during those activities of a patient in which deep flexion is not typically obtained.

In a typical orthopaedic knee prosthesis, paradoxical anterior translation may occur whenever the knee prosthesis is positioned at a degree of flexion greater than zero degrees. The likelihood of anterior translation generally increases as the orthopaedic knee prosthesis is articulated to larger degrees of flexion, particularly in the mid-flexion range. In such orientations, paradoxical anterior translation of the femoral component on the tibial bearing can occur whenever the tangential (traction) force between the femoral component and the tibial bearing fails to satisfy the following equation:

$$T < \mu N \tag{1}$$

wherein "T" is the tangential (traction) force, "$\mu$" is the coefficient of friction of the femoral component and the tibial bearing, and "N" is the normal force between the femoral component and the tibial bearing. As a generalization, the tangential (traction) force between the femoral component and the tibial bearing can be defined as $$T = M/R \tag{2}$$

wherein "T" is the tangential (traction) force between the femoral component and the tibial bearing, "M" is the knee moment, and "R" is the radius of curvature in the sagittal plane of the condyle surface in contact with the tibial bearing at the particular degree of flexion. It should be appreciated that equation (2) is a simplification of the governing real-world equations, which does not consider such other factors as inertia and acceleration. Regardless, the equation (2) provides insight that paradoxical anterior translation of an orthopaedic knee prosthesis may be reduced or delayed by controlling the radius of curvature of the condyle surface of the femoral component. That is, by controlling the radius of curvature of the condyle surface (e.g., increasing or maintaining the radius of curvature), the right-hand side of equation (2) may be reduced, thereby decreasing the value of the tangential (traction) force and satisfying the equation (1). As discussed above, by ensuring that the tangential (traction) force satisfies equation (1), paradoxical anterior translation of the femoral component on the tibial bearing may be reduced or otherwise delayed to a greater degree of flexion.

Based on the above analysis, to reduce or delay the onset of paradoxical anterior translation, the geometry of the condyle surface 100 of one or both of the condyles 52, 54 of the femoral component 12 is controlled. For example, in some embodiments, the radius of curvature of the condyle surface 100 is controlled such that the radius of curvature is held constant over a range of degrees of flexion and/or is increased in the early to mid flexion ranges. Comparatively, typical femoral components have decreasing radii of curvatures beginning at the distal radius of curvature (i.e., at about 0 degrees of flexion). However, it has been determined that by maintaining a relatively constant radius of curvature (i.e., not decreasing the radius of curvature) over a predetermined range of degrees of early to mid-flexion and/or increasing the radius of curvature over the predetermined range of degrees of flexion may reduce or delay paradoxical anterior translation of the femoral component 12.

Additionally, in some embodiments, the condyle surface 100 is configured or designed such that the transition between discrete radii of curvature of the condyle surface 100 is gradual. That is, by gradually transitioning between the discrete radii of curvature, rather than abrupt transitions, paradoxical anterior translation of the femoral component 12 may be reduced or delayed. Further, in some embodiments, the rate of change in the radius of curvature of the condyle surface in the early to mid flexion ranges (e.g., from about 0 degrees to about 90 degrees) is controlled such that the rate of change is less than a predetermined threshold. That is, it has been determined that if the rate of change of the radius of curvature of the condyle surface 100 is greater than the predetermined threshold, paradoxical anterior translation may occur.

Accordingly, in some embodiments as illustrated in FIGS. 6-12, the condyle surface 100 of the femoral component 12 has an increased radius of curvature in early to middle degrees of flexion. By increasing the radius of curvature, paradoxical anterior translation may be reduced or delayed to a later degree of flexion. The amount of increase between the radius of curvature R2 and the radius of curvature R3 (see FIGS. 6 and 7), as well as, the degree of flexion on the condyle surface 100 at which such increase occurs has been determined to affect the occurrence of paradoxical anterior translation. As discussed in more detail in the U.S. patent application Ser. No. 12/165,579, entitled "Orthopaedic Femoral Prosthesis Having Controlled Condylar Curvature", which was filed concurrently herewith and is hereby incorporated by reference, multiple simulations of various femoral component designs were performed using the Life-MOD/Knee Sim, version 1007.1.0 Beta 16 software program, which is commercially available from LifeModeler, Inc. of San Clemente, Calif., to analyze the effect of increasing the radius of curvature of the condyle surface of the femoral components in early and mid flexion. Based on such analysis, it has been determined that paradoxical anterior translation of the femoral component relative to the tibial bearing may be reduced or otherwise delayed by increasing the radius of curvature of the condyle surface by an amount in the range of about 0.5 millimeters to about 5 millimeters or more at a degree of flexion in the range of about 30 degrees of flexion to about 90 degrees of flexion.

Figure 8:
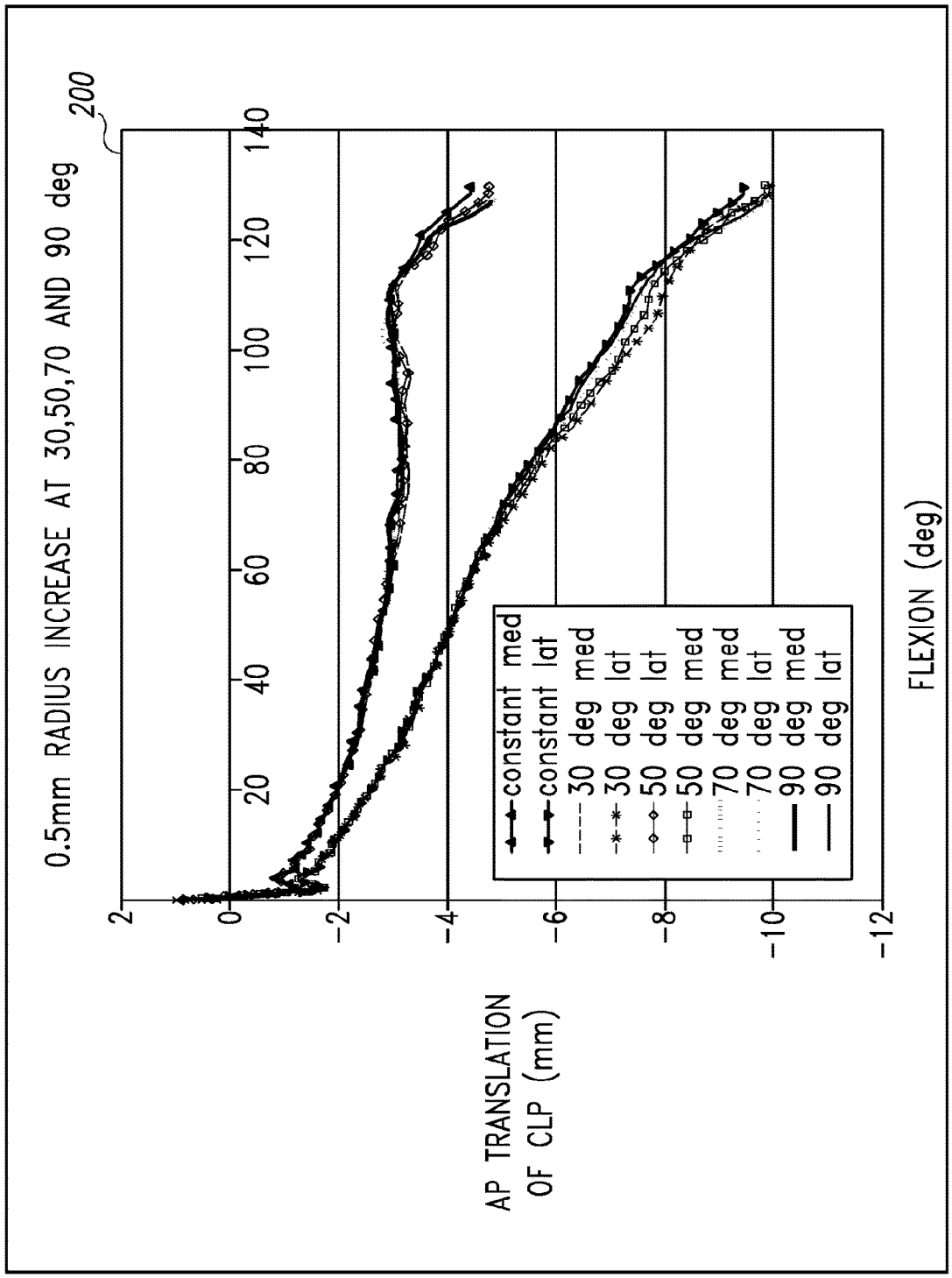
FIG. 8 is a graph of the anterior-posterior translation of a simulated femoral component having an increased radius of curvature located at various degrees of flexion.
Figure 9:
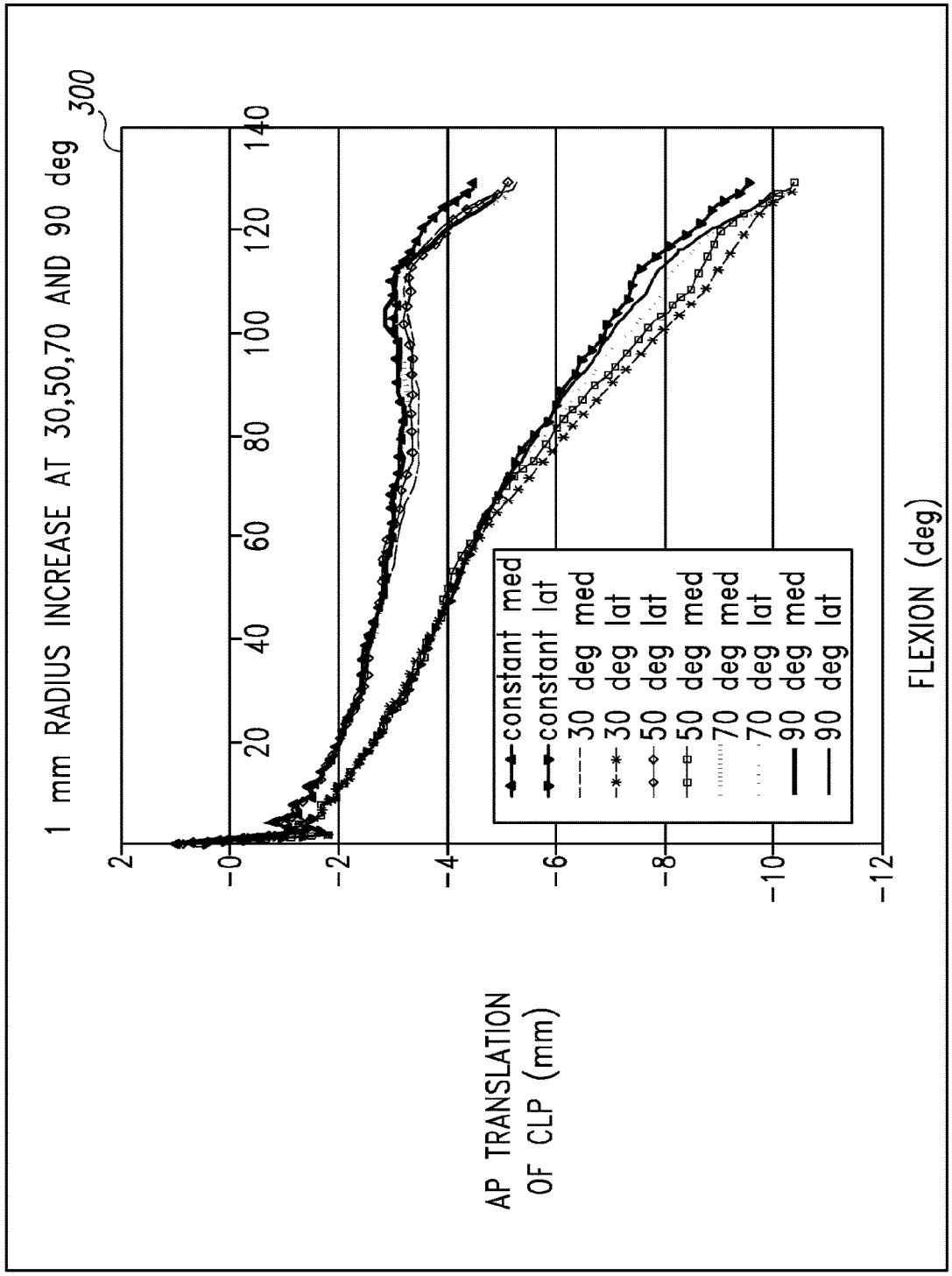
FIG. 9 is a graph of the anterior-posterior translation of another simulated femoral component having an increased radius of curvature located at various degrees of flexion.
Figure 10:
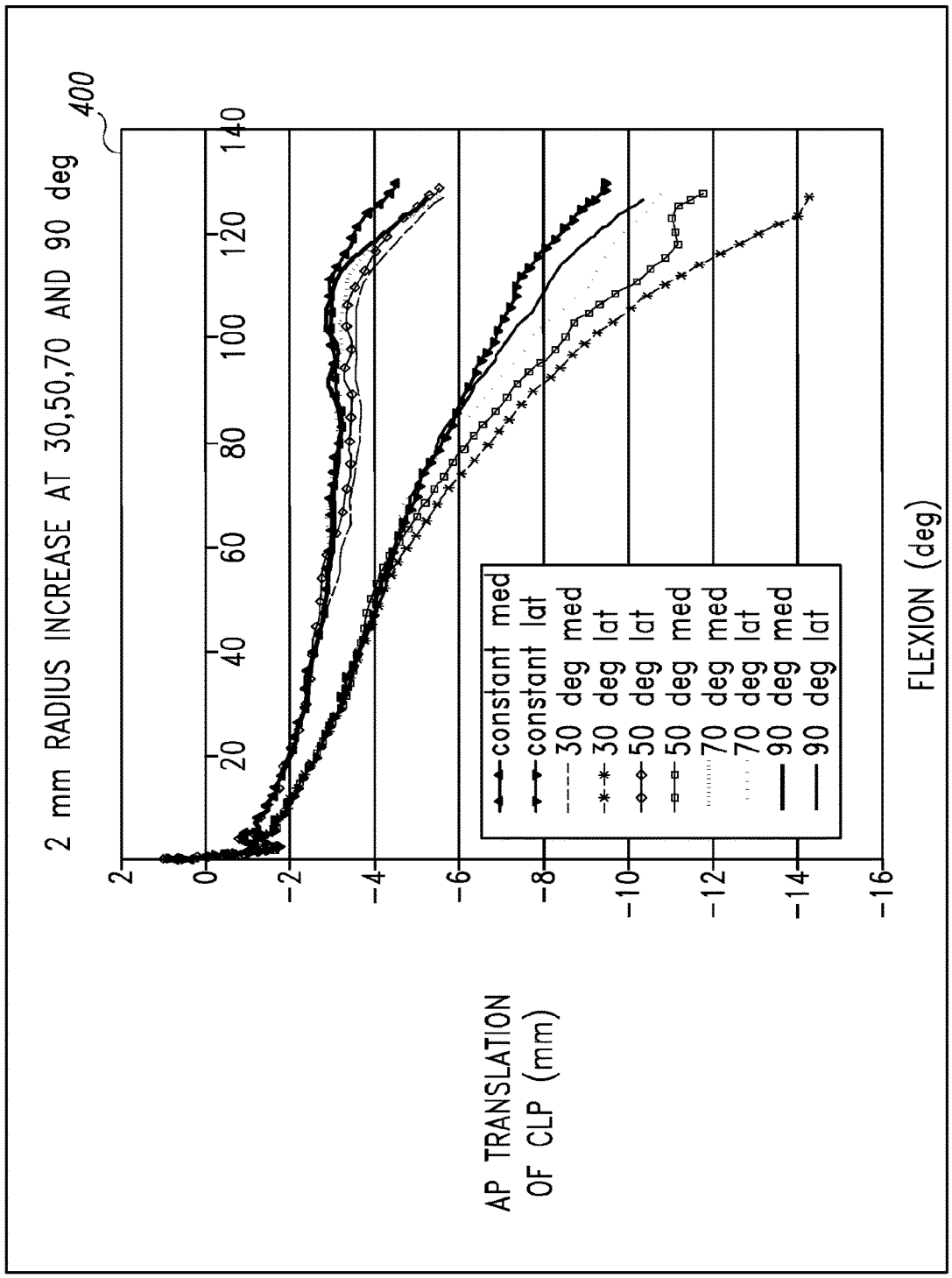
FIG. 10 is a graph of the anterior-posterior translation of another simulated femoral component having an increased radius of curvature located at various degrees of flexion.
Figure 11:
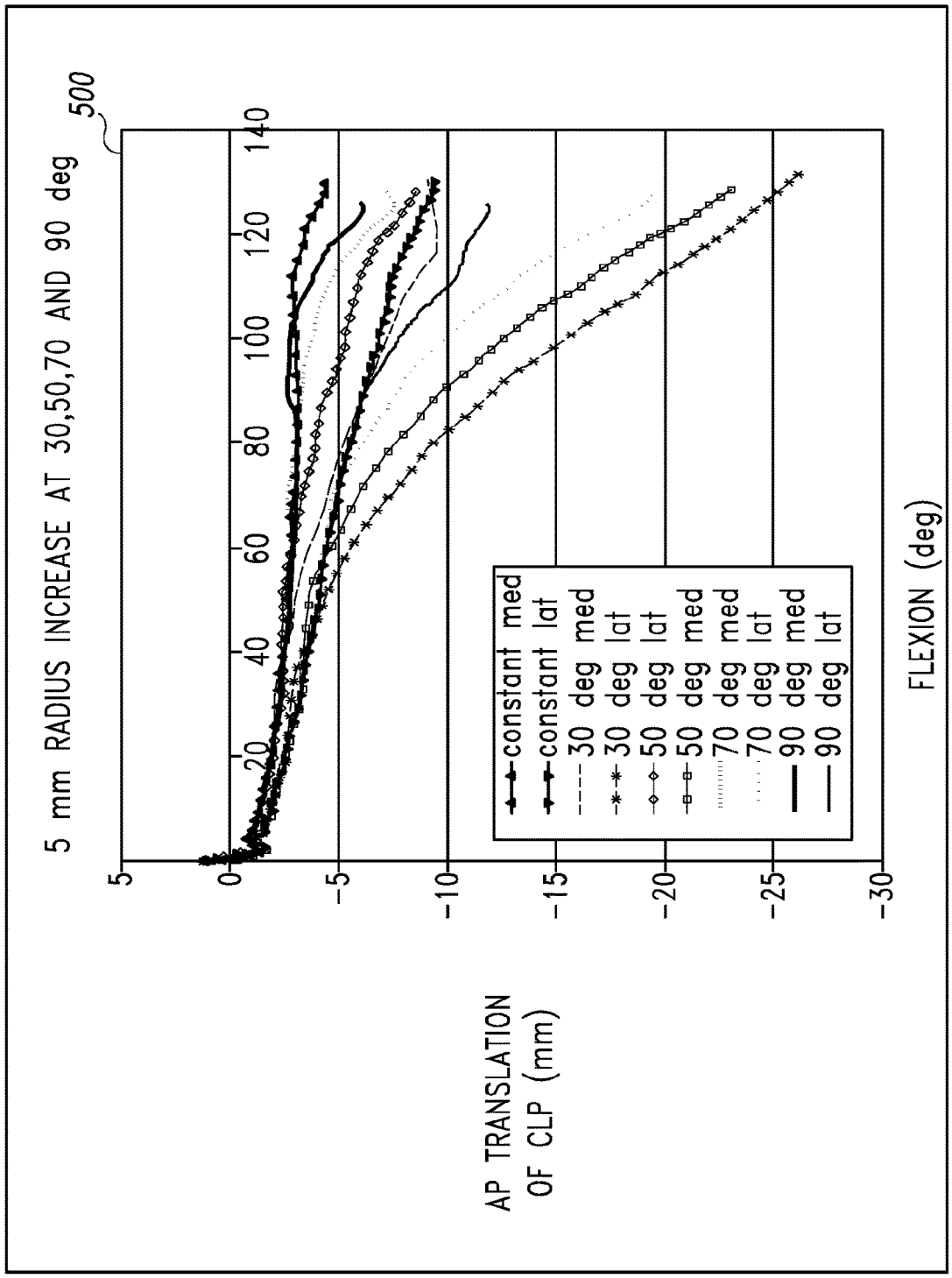
FIG. 11 is a graph of the anterior-posterior translation of another simulated femoral component having an increased radius of curvature located at various degrees of flexion.

For example, the graph 200 illustrated in FIG. 8 presents the results of a deep bending knee simulation using a femoral component wherein the radius of curvature of the condyle surface is increased by 0.5 millimeters (i.e., from 25.0 millimeters to 25.5 millimeters) at 30 degrees of flexion, at 50 degrees of flexion, at 70 degrees of flexion, and at 90 degrees of flexion. Similarly, the graph 300 illustrated in FIG. 9 presents the results of a deep bending knee simulation using a femoral component wherein the radius of curvature of the condyle surface is increased by 1.0 millimeters (i.e., from 25.0 millimeters to 26.0 millimeters) at 30 degrees of flexion, at 50 degrees of flexion, at 70 degrees of flexion, and at 90 degrees of flexion. The graph 400 illustrated in FIG. 10 presents the results of a deep bending knee simulation using a femoral component wherein the radius of curvature of the condyle surface is increased by 2.0 millimeters (i.e., from 25.0 millimeters to 27.0 millimeters) at 30 degrees of flexion, at 50 degrees of flexion, at 70 degrees of flexion, and at 90 degrees of flexion. Additionally, the graph 500 illustrated in FIG. 11 presents the results of a deep bending knee simulation using a femoral component wherein the radius of curvature of the condyle surface is increased by 5.0 millimeters (i.e., from 25.0 millimeters to 26.0 millimeters) at 30 degrees of flexion, at 50 degrees of flexion, at 70 degrees of flexion, and at 90 degrees of flexion.

In the graphs 200, 300, 400, 500, the condylar lowest or most distal points (CLP) of the medial condyle ("med") and the lateral condyle ("lat") of the femoral component are graphed as a representation of the relative positioning of the femoral component to the tibial bearing. As such, a downwardly sloped line represents roll-back of the femoral component on the tibial bearing and an upwardly sloped line represents anterior translation of the femoral component on the tibial bearing.

As illustrated in the graphs 200, 300, 400, 500, anterior sliding of the femoral component was delayed until after about 100 degrees of flexion in each of the embodiments; and the amount of anterior translation was limited to less than about 1 millimeter. In particular, "roll-back" of the femoral component on the tibial bearing was promoted by larger increases in the radius of curvature of the condyle surface at earlier degrees of flexion. Of course, amount of increase in the radius of curvature and the degree of flexion at which such increase is introduced is limited by other factors such as the anatomical joint space of the patient's knee, the size of the tibial bearing, and the like. Regardless, based on the simulations reported in the graphs 200, 300, 400, 500, paradoxical anterior translation of the femoral component on the tibial bearing can be reduced or otherwise delayed by increasing the radius of curvature of the condyle surface of the femoral component during early to mid flexion.

Accordingly, referring back to FIGS. 6 and 7, the condyle surface 100 in the sagittal plane is formed in part from a number of curved surface sections 102, 104, 106, 108, the sagittal ends of each of which are tangent to the sagittal ends of any adjacent curved surface section of the condyles surface 100. Each curved surface section 102, 106, 108 is defined by a radius of curvature. In particular, the curved surface section 102 is defined by a radius of curvature R1, the curved surface section 106 is defined by a radius of curvature R3, and the curved surface section 108 is defined by a radius of curvature R4. In addition, as discussed in more detail below, the curved surface section 104 is designed to provide a gradual transition from the first radius of curvature R1 to a second radius of curvature R2. To do so, the curved surface section 104 is defined by a plurality of curved surface sections 110, 120, each of which is defined by a separate radius of curvature R5.

As discussed above, the condyle surface 100 of the femoral component 12 is configured such that the radius of curvature R3 of the curved surface section 106 is greater than the radius of curvature R2 of the curved surface section 104. In one embodiment, the radius of curvature R3 is greater than the radius of curvature R2 by 0.5 millimeters or more. In another embodiment, the radius of curvature R3 is greater than the radius of curvature R2 by 2 millimeters or more. In another embodiment, the radius of curvature R3 is greater than the radius of curvature R2 by 2 millimeters or more. In a particular embodiment, the radius of curvature R3 is greater than the radius of curvature R2 by at least 5 millimeters or more. It should be appreciated, however, that the particular increase of radius of curvature between R2 and R3 may be based on or scaled to the particular size of the femoral component 12 in some embodiments.

Each of the curved surface sections 102, 104, 106, 108 contacts the bearing surface 42 (or 44) of the tibial bearing 14 through different ranges of degrees of flexion. For example, the curved surface section 102 extends from an earlier degree of flexion θ1 to a later degree of flexion θ2. The curved surface section 104 extends from the degree of flexion θ2 to a later degree of flexion θ3. The curved surface section 106 extends from the degree of flexion θ3 to a later degree of flexion θ4.

For example, in one embodiment, the curved surface section 102 may extend from a degree of flexion θ1 of about −10 degrees (i.e., 10 degrees of hyperextension) to a degree of flexion θ2 of about 5 degrees of flexion. The curved surface section 104 extends from the degree of flexion θ2 of about 5 degrees of flexion to a degree of flexion θ3 of about 65 degrees of flexion. The curved surface section 106 extends from the degree of flexion θ3 of about 65 degrees of flexion to a degree of flexion θ4 of about 90 degrees of flexion and the curved surface section 108 extends from the degree of flexion θ4 of about 90 degrees of flexion to a degree of flexion θ5 of about 104 degrees of flexion.

It should be appreciated, however, that each of the curved surface sections 102, 104, 106, 108 may extend from degrees of flexion different from those discussed above. For example, the particular degrees of flexion through which the curved surface sections 102, 104, 106, 108 extend may be based or otherwise determined based on the type of femoral component 12 (e.g., cruciate-retaining or posterior stabilized), the size of the femoral component 12, and/or the like.

As discussed above, the curved surface section 104 is designed to gradually transition from the radius of curvature R1 to the radius of curvature R2. To do so, in one embodiment as illustrated in FIG. 5, the curved surface section 104 is defined by a plurality of curved surface sections 110. In the illustrative embodiment of FIG. 5, the curved surface section 104 is defined by six curved surface sections 110A, 110B, 110C, 110D, 110E, 110F, but may be defined by or otherwise include more or less curved surface sections 110 in other embodiments. The particular number of curved surface sections 110 used may be based on, for example, the size of the angle subtended by the curved surface section 104.

Each of the curved surface sections 110 of the condyle surface 100 contacts the bearing surface 42 (or 44) of the tibial bearing 14 through different ranges of degrees of flexion. For example, the curved surface section 110A extends from the degree of flexion θ2 to a later degree of flexion θC1, the curved surface section 110B extends from the degree of flexion θC1 to a later degree of flexion θC2, the curved surface section 110C extends from the degree of flexion θC2 to a later degree of flexion θC3, the curved surface section 110D extends from the degree of flexion θC3 to a later degree of flexion θC4, the curved surface section 110E extends from the degree of flexion θC4 to a later degree of flexion θC5, and the curved surface section 110F extends from the degree of flexion θC5 to the later degree of flexion θ3.

Figure 6:
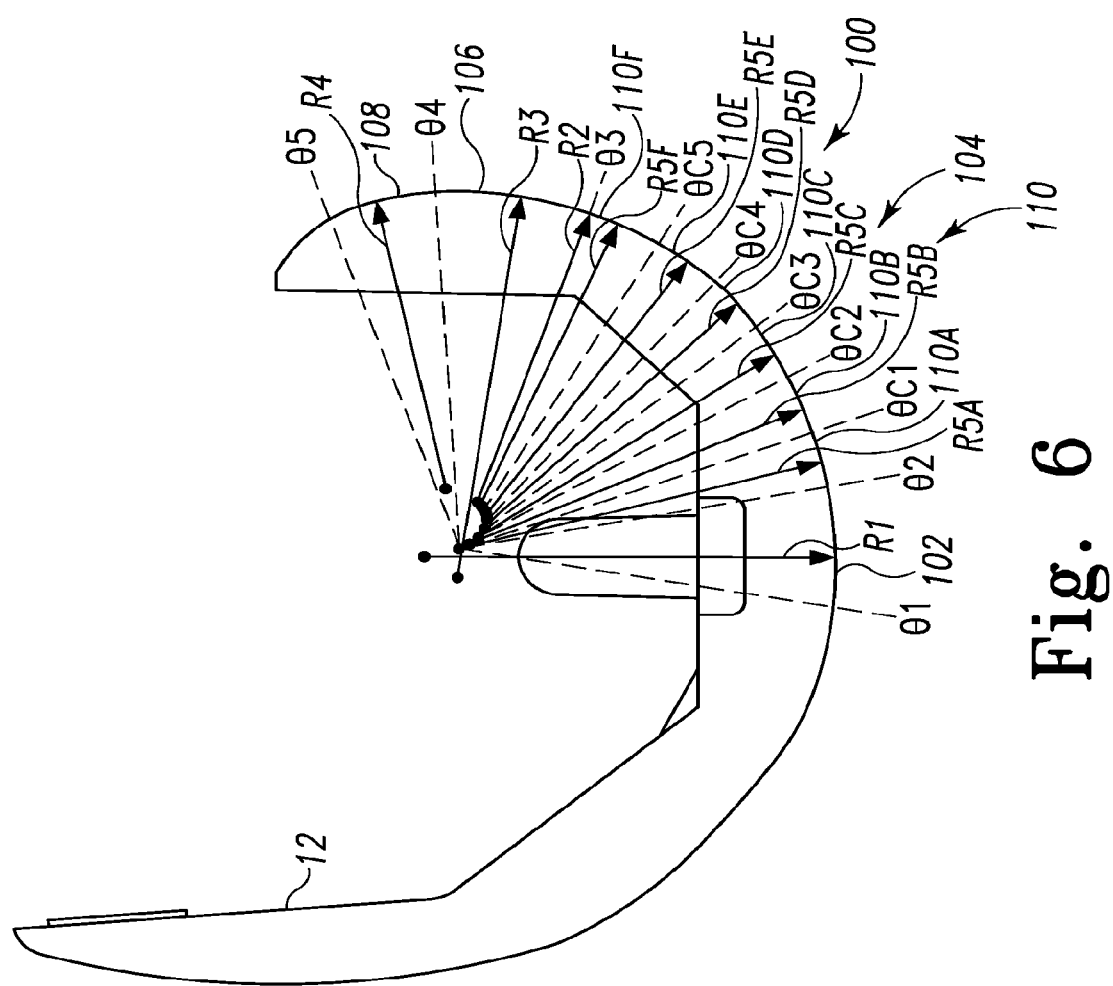
FIG. 6 is a cross-sectional view of another embodiment of the femoral component of FIG. 1.

In the illustrative embodiment of FIG. 6, each of the curved surface sections 110 extend substantially equal degrees of flexion. That is, the degrees of flexion between θ2 and θC1, θC1 and θC2, between θC2 and θC3, between θC3 and θC4, between θC4 and θC5, and between θC5 and θ3 are substantially equal. In one particular embodiment, each curved surface section 110 extends for about 10 degrees. However, in other embodiments, each curved surface section 110 may extend a greater or lesser amount. In particular, in one embodiment, each curved surface section extend (i.e., subtend an angle) from about 1 degree to about 15 degrees.

Each of the curved surface sections 110 is defined by a radius of curvature R5. That is, the curved surface section 110A is defined by a radius of curvature R5A, the curved surface section 110B is defined by a radius of curvature R5B, the curved surface section 110C is defined by a radius of curvature R5C, the curved surface section 110D is defined by a radius of curvature R5D, the curved surface section 110E is defined by a radius of curvature R5E, and the curved surface section 110F is defined by a radius of curvature R5F. Each radius of curvature R5 is smaller (i.e., has a shorter length) than the anteriorly-adjacent radius of curvature R5. That is, R5F is smaller than R5E, R5E is smaller than R5D, R5D is smaller than R5C, R5C is smaller than R5B, and R5B is smaller than R5A. For example, in one embodiment, each radius of curvature R5 may have a length shorter than the anteriorly-adjacent radius of curvature R5 by an amount in the range of about 0.1 millimeters to about 5 millimeters. However, in other embodiments, each radius of curvature R5 may have a length shorter than the anteriorly-adjacent radius of curvature R5 by an amount greater or less than such values. The particular length of each radius of curvature R5 may be determined based on the particular application, the length of the curved surface section 104, an defined equation, and/or the like.

Figure 7:
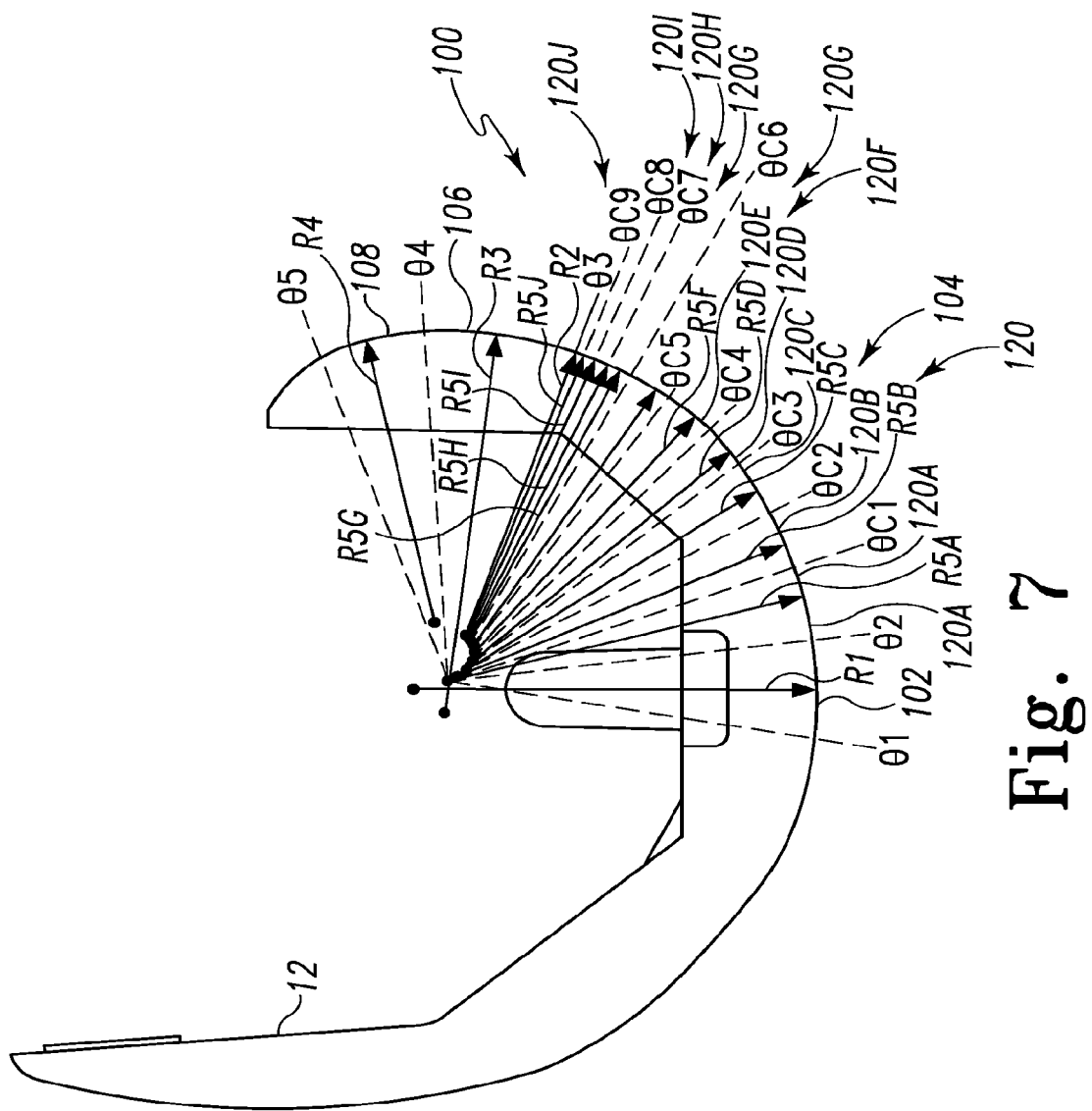
FIG. 7 is a cross-sectional view of another embodiment of the femoral component of FIG. 1.

Referring now to FIG. 7, in another embodiment, the curved surface section 104 may be formed by a plurality of curved surface sections 120, each of which may extend a different amount of degrees (i.e., subtend angles of different sizes). For example, in the illustrative embodiment of FIG. 7, the curved surface section 104 is defined by ten curved surface sections 120A, 120B, 120C, 120D, 120E, 120F, 120G, 120H, 120I, 120J. The curved surface section 120A extends from the degree of flexion θ1 to a later degree of flexion θC1, the curved surface section 120B extends from the degree of flexion θC1 to a later degree of flexion θC2, the curved surface section 120C extends from the degree of flexion θC2 to a later degree of flexion θC3, the curved surface section 120D extends from the degree of flexion θC3 to a later degree of flexion θC4, the curved surface section 120E extends from the degree of flexion θC4 to a later degree of flexion θC5, the curved surface section 120F extends from the degree of flexion θC5 to a later degree of flexion θC6, the curved surface section 120G extends from the degree of flexion θC6 to a later degree of flexion θC7, the curved surface section 120H extends from the degree of flexion θC7 to a later degree of flexion θC8, the curved surface section 120I extends from the degree of flexion θC8 to a later degree of flexion θC9, and the curved surface section 120J extends from the degree of flexion θC9 to the later degree of flexion θ3.

As discussed above, each of the curved surface sections 120 extend different degrees of flexion. That is, the degrees of flexion between θ2 and θC1, θC1 and θC2, between θC2 and θC3, between θC3 and θC4, between θC4 and θC5, between θC5 and θC6, between θC6 and θC7, between θC7 and θC8, between θC8 and θC9, and between θC9 and θ3 are different from each other. In some embodiments, each curved surface section 120 subtends an angle that is less than the angle subtended by the anteriorly-adjacent section 120. For example, in the illustrative embodiment of FIG. 7, the curved surface section 120A extends for about 10 degrees, the curved surface section 120B extends for about 9 degrees, the curved surface section 120C extends for about 8 degrees, the curved surface section 120D extends for about 7 degrees, the curved surface section 120E extends for about 6 degrees, the curved surface section 120F extends for about 5 degrees, the curved surface section 120G extends for about 4 degrees, the curved surface section 120H extends for about 3 degrees, the curved surface section 120I extends for about 2 degrees, and the curved surface section 120J extends for about 1 degree.

Although each curved surface section 120 subtends an angle 1 degree less than the anteriorly-adjacent section 120 in the illustrative embodiment of FIG. 7, the curved surface sections 120 may subtend angles that are less than the anteriorly adjacent section 120 by an amount greater than 1 degree in other embodiments. Additionally, in other embodiments, each curved surface section 120 may subtend an angle that is greater than the angle subtended by the anteriorly-adjacent section 120. For example, each curved surface section 120 may subtend an angle that is greater than the angle subtended by the anteriorly-adjacent section 120 by about 0.5, 1, or more degrees in some embodiments. Further, in some embodiments, each of the curved surface sections 120 may subtend angles of various sizes. That, each curved surface section 120 may be greater than or less than the anteriorly-adjacent curved surface 120 in some embodiments.

The overall shape and design of the condyle surface 100 of the femoral component 12 has been described above in regard to a single condyle 52, 54 of the femoral component 12. It should be appreciated that in some embodiments both condyles 52, 54 of the femoral component 12 may be symmetrical and have similar condyle surfaces 100. However, in other embodiments, the condyles 52, 54 of the femoral component 12 may be asymmetrical. That is, each condyle 52, 54 may have a condyle surface 100 having the features described herein but being asymmetrical to the other condyle 52, 54.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic knee prosthesis comprising:
a femoral component having a condyle surface curved in the sagittal plane; and
a tibial bearing having a bearing surface configured to articulate with the condyle surface of the femoral component,
wherein the condyle surface (i) contacts the bearing surface at a first contact point on the condyle surface at a first degree of flexion less than about 30 degrees, (ii) contacts the bearing surface at a second contact point on the condyle surface at a second degree of flexion greater than about 45 degrees, and (iii) contacts the bearing surface at a third contact point on the condyle surface at a third degree of flexion greater than the second degree of flexion,
wherein the condyle surface in the sagittal plane has a first radius of curvature at the first contact point, a second radius curvature at the second contact point, and a third radius of curvature at the third contact point, the third radius of curvature being different from the second radius of curvature and,
wherein the condyle surface in the sagittal plane between the first contact point and the second contact point includes a plurality of curved surface sections, and wherein each succeeding curved surface section of the plurality of curved surface section has a radius of curvature less than a radius of curvature of an anteriorly-adjacent preceding curved surface section between the first contact point and the second contact point of the condyle surface.

2. The orthopaedic knee prosthesis of claim 1, wherein the first degree of flexion is in the range of 0 degrees to 10 degrees, the second degree of flexion is in the range of 60 degrees to 70 degrees, and the third degree of flexion is in the range of 80 degrees to 110 degrees.

3. The orthopaedic knee prosthesis of claim 2, wherein the first degree of flexion is about 5 degrees, the second degree of flexion is about 65 degrees, and the third degree of flexion is about 90 degrees.

4. The orthopaedic knee prosthesis of claim 1, wherein the plurality of curved surface sections includes an anterior-most curved surface section, the radius of curvature of the anterior-most curved surface section having a length greater than the radius of curvature of any other curved surface section of the plurality of curved surface sections.

5. The orthopaedic knee prosthesis of claim 1, wherein the length of the radius of curvature of each curved surface section posterior to the anterior-most curved surface section is less than the length of the radius of curvature of an anteriorly-adjacent curved surface section by a distance in the range of 0.1 millimeters to 5 millimeters.

6. The orthopaedic knee prosthesis of claim 1, wherein the length of the radius of curvature of each curved surface section posterior to the anterior-most curved surface section is less than the length of the radius of curvature of an anteriorly-adjacent curved surface section by a distance in the range of 1 millimeters to 3 millimeters.

7. The orthopaedic knee prosthesis of claim 1, wherein the length of the radius of curvature of each curved surface section posterior to the anterior-most curved surface section is less than the length of the radius of curvature of an anteriorly-adjacent curved surface section by about 1 millimeter.

8. The orthopaedic knee prosthesis of claim 1, wherein each of the plurality of curved surface sections subtends a corresponding angle, each angle subtended by the plurality of curved surface sections being approximately equal.

9. The orthopaedic knee prosthesis of claim 1, wherein (i) the plurality of curved surface sections includes an anterior-most curved surface section and (ii) each of the plurality of curved surface sections subtends a corresponding angle, the angle subtended by each of the curved surface sections posterior to the anterior-most curved surface section being less than the angle subtended by an anteriorly-adjacent curved surface section.

10. The orthopaedic knee prosthesis of claim 9, wherein the angle subtended by each of the curved surface sections posterior to the anterior-most curved surface section is less than the angle subtended by the anteriorly-adjacent curved surface section by an amount in the range of 0.5 degrees to 5 degrees.

11. The orthopaedic knee prosthesis of claim 1, wherein (i) the plurality of curved surface sections includes an anterior-most curved surface section and (ii) each of the plurality of curved surface sections subtends a corresponding angle, the angle subtended by each of the curved surface sections posterior to the anterior-most curved surface section being greater than the angle subtended by an anteriorly-adjacent curved surface section.

12. The orthopaedic knee prosthesis of claim 11, wherein the angle subtended by each of the curved surface sections posterior to the anterior-most curved surface section is greater than the angle subtended by the anteriorly-adjacent curved surface section by an amount in the range of 0.5 degrees to 5 degrees.

\* \* \* \* \*